(12) United States Patent
Tanaka et al.

(10) Patent No.: US 11,736,092 B2
(45) Date of Patent: Aug. 22, 2023

(54) PHASE ADJUSTMENT CIRCUIT AND ENDOSCOPE SYSTEM

(71) Applicant: OLYMPUS CORPORATION, Hachioji (JP)

(72) Inventors: Takanori Tanaka, Tokyo (JP); Shuzo Hiraide, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/893,832

(22) Filed: Aug. 23, 2022

(65) Prior Publication Data

US 2022/0407501 A1 Dec. 22, 2022

Related U.S. Application Data

(63) Continuation of application No. PCT/JP2020/009306, filed on Mar. 5, 2020.

(51) Int. Cl.
| *H03L 7/081* | (2006.01) |
| *H03H 11/16* | (2006.01) |
| *G11C 7/22* | (2006.01) |

(52) U.S. Cl.
CPC .......... *H03H 11/16* (2013.01); *H03L 7/0814* (2013.01); *G11C 7/222* (2013.01)

(58) Field of Classification Search
None
See application file for complete search history.

(56) References Cited

U.S. PATENT DOCUMENTS

| 6,917,388 B2 * | 7/2005 | Naka | ................. H04N 5/20 348/E5.073 |
| 2003/0184677 A1 * | 10/2003 | Kuzumoto | ........... H04N 7/0352 348/465 |

FOREIGN PATENT DOCUMENTS

| JP | 6-311154 A | 11/1994 |
| JP | 8-23272 A | 1/1996 |
| JP | 11-505987 A | 5/1999 |
| JP | 2003-198874 A | 7/2003 |
| JP | 2009-147916 A | 7/2009 |
| WO | 96/37952 A1 | 11/1996 |

OTHER PUBLICATIONS

International Search Report dated May 12, 2020, issued in counterpart International Application No. PCT/JP2020/009306, with English Translation. (4 pages).

* cited by examiner

*Primary Examiner* — Cassandra F Cox
(74) *Attorney, Agent, or Firm* — WHDA, LLP

(57) ABSTRACT

In a phase adjustment circuit, a binary circuit is configured to output a binary signal on the basis of an edge of a video signal. A phase-delayed clock signal generation circuit is configured to generate a phase-delayed clock signal having a later phase than a phase of a clock signal by a first delay amount. A delay time control circuit is configured to cause a phase of the binary signal and the phase of the phase-delayed clock signal to match each other by adjusting the first delay amount. A sampling signal generation circuit is configured to generate a sampling signal having a later phase than the phase of the clock signal by a second delay amount. The second delay amount is in accordance with both a phase shift amount, which is based on the clock signal, and the first delay amount.

12 Claims, 19 Drawing Sheets

PHASE ADJUSTMENT CIRCUIT AND ENDOSCOPE SYSTEM

The present application is a continuation application based on International Patent Application No. PCT/JP2020/009306 filed on Mar. 5, 2020, the content of which is incorporated herein by reference.

BACKGROUND OF THE INVENTION

Field of the Invention

The present invention relates to a phase adjustment circuit and an endoscope system.

Description of Related Art

FIG. 18 shows a configuration of an endoscope system 1001 of the prior art. The endoscope system 1001 shown in FIG. 18 includes a camera unit 1009, an analog front end (AFE) 1050, and a processor 1006.

The camera unit 1009 generates a video signal and transmits the video signal to the AFE 1050. The camera unit 1009 includes an image sensor 1090 and a transmission circuit 1091. The AFE 1050 captures the video signal transmitted by the camera unit 1009 and performs signal processing on the video signal. The AFE 1050 includes a phase adjustment circuit 1051 and an analog-to-digital converter (ADC) 1052. The processor 1006 generates a necessary signal for an operation of each of the camera unit 1009 and the AFE 1050. The processor 1006 includes an oscillator 1060 and a signal generation circuit 1061.

The image sensor 1090 includes a plurality of pixels disposed in a matrix shape. The image sensor 1090 performs imaging in accordance with a clock signal and a synchronization signal output from the processor 1006 and outputs an analog video signal to the transmission circuit 1091. The transmission circuit 1091 transmits the video signal to the AFE 1050. The video signal is transferred to the AFE 1050 by a cable 1300.

The oscillator 1060 generates the clock signal. The signal generation circuit 1061 generates a sampling signal and a synchronization signal on the basis of the clock signal. In addition, the signal generation circuit 1061 generates an adjustment signal used for adjusting the phase of the sampling signal. The processor 1006 outputs the sampling signal and the adjustment signal to the phase adjustment circuit 1051 and transmits the clock signal and the synchronization signal to the camera unit 1009. The clock signal is transferred to the camera unit 1009 by a cable 1301. The synchronization signal is transferred to the camera unit 1009 by a cable 1302.

The clock signal is transferred to the camera unit 1009 by the cable 1301, and the video signal generated by the image sensor 1090 is transferred to the AFE 1050 by the cable 1300. A signal is delayed in the cable 1301, the image sensor 1090, and the cable 1300. Therefore, a phase difference occurs between the video signal and the sampling signal. The phase adjustment circuit 1051 adjusts the phase of the sampling signal on the basis of the adjustment signal. The phase adjustment circuit 1051 outputs the sampling signal having the adjusted phase to the ADC 1052.

The ADC 1052 performs AD conversion. The ADC 1052 captures the video signal at a timing indicated by the sampling signal and converts the analog video signal into a digital video signal. The ADC 1052 outputs the digital video signal to the processor 1006.

FIG. 19 shows waveforms of the clock signal, the video signal, and the sampling signal. The horizontal direction in FIG. 19 indicates time, and the vertical direction in FIG. 19 indicates a voltage of each signal.

The video signal includes a standard signal SIG11 and a pixel signal SIG12. The standard signal SIG11 and the pixel signal SIG12 appear one after the other. The phase of the video signal is later than that of the clock signal by a delay amount DL11.

The sampling signal is synchronized with the clock signal. The phase adjustment circuit 1051 delays the phase of the sampling signal by a shift amount pH11 in order to capture the video signal at a timing at which the voltage of the standard signal SIG11 is stable and at a timing at which the voltage of the pixel signal SIG12 is stable. In FIG. 19, the sampling signal input into the phase adjustment circuit 1051 and the sampling signal having the phase adjusted by the phase adjustment circuit 1051 are shown. The ADC 1052 captures the standard signal SIG11 at a timing T11 at which the sampling signal falls and captures the pixel signal SIG12 at a timing T12 at which the sampling signal rises.

An invention related to a circuit that generates a sampling clock is disclosed in Japanese Unexamined Patent Application, First Publication No. 2009-147916. The circuit generates the sampling clock on the basis of a synchronization signal embedded in a video signal.

SUMMARY OF THE INVENTION

According to a first aspect of the present invention, a phase adjustment circuit is configured to generate a sampling signal used for capturing a video signal at a later timing than a timing indicated by a clock signal. The phase adjustment circuit includes a binary circuit, a phase-delayed clock signal generation circuit, a delay time control circuit, and a sampling signal generation circuit. The binary circuit is configured to detect an edge of the video signal and output a binary signal having a voltage that changes at a timing of the detected edge. The phase-delayed clock signal generation circuit is configured to generate a phase-delayed clock signal having a later phase than a phase of the clock signal by a first delay amount. The delay time control circuit is configured to cause a phase of the binary signal and the phase of the phase-delayed clock signal to match each other by adjusting the first delay amount on the basis of the binary signal and the phase-delayed clock signal. The sampling signal generation circuit is configured to generate the sampling signal having a later phase than the phase of the clock signal by a second delay amount. The second delay amount is in accordance with both a phase shift amount, which is based on the timing indicated by the clock signal, and the first delay amount adjusted by the delay time control circuit.

According to a second aspect of the present invention, in the first aspect, the sampling signal generation circuit may be configured to receive the clock signal and generate the sampling signal by adding the second delay amount to the clock signal. The phase-delayed clock signal generation circuit may be configured to receive the sampling signal generated by the sampling signal generation circuit and generate the phase-delayed clock signal by changing the phase of the sampling signal by the shift amount.

According to a third aspect of the present invention, in the first aspect, the phase-delayed clock signal generation circuit may be configured to receive the clock signal and generate the phase-delayed clock signal by adding the first delay amount to the clock signal. The sampling signal generation circuit may be configured to receive the phase-delayed clock signal generated by the phase-delayed clock signal generation circuit and generate the sampling signal by changing the phase of the phase-delayed clock signal by the shift amount.

According to a fourth aspect of the present invention, in the first aspect, the sampling signal generation circuit may be configured to receive the clock signal having a higher frequency than a frequency of the video signal and generate the sampling signal having almost the same frequency as the frequency of the video signal by adding the second delay amount to the clock signal and by reducing the frequency of the clock signal. The phase-delayed clock signal generation circuit may be configured to receive the sampling signal generated by the sampling signal generation circuit and generate the phase-delayed clock signal by changing the phase of the sampling signal by the shift amount by using a shift register.

According to a fifth aspect of the present invention, in the first aspect, the phase adjustment circuit may further include a delay circuit. The delay circuit is configured to receive the phase-delayed clock signal generated by the phase-delayed clock signal generation circuit. The delay circuit is configured to add a third delay amount to the phase-delayed clock signal. The third delay amount is a difference between a phase of the video signal input into the binary circuit and a phase of the binary signal. The delay circuit is configured to output the phase-delayed clock signal to which the third delay amount has been added to the delay time control circuit.

According to a sixth aspect of the present invention, in the first aspect, the sampling signal generation circuit may be configured to output the sampling signal to a video-signal-capturing circuit configured to capture the video signal on the basis of the sampling signal. The phase adjustment circuit may further include a delay circuit. The delay circuit is configured to add a third delay amount to the video signal. The third delay amount is a difference between a phase of the video signal input into the binary circuit and a phase of the binary signal. The delay circuit is configured to output the video signal to which the third delay amount has been added to the video-signal-capturing circuit.

According to a seventh aspect of the present invention, in the first aspect, the video signal may include a reference signal transmitted in a blanking period. The binary circuit may be configured to detect the edge of the video signal by using the reference signal.

According to an eighth aspect of the present invention, in the first aspect, the video signal may include a first signal having a predetermined voltage and a second signal having a voltage that fluctuates. The first signal and the second signal appear one after the other.

According to a ninth aspect of the present invention, in the first aspect, the phase adjustment circuit may further include a memory configured to store digital information indicating the first delay amount when the delay time control circuit causes the phase of the binary signal and the phase of the phase-delayed clock signal to match each other. The phase-delayed clock signal generation circuit may include a first digital-controlled delay circuit configured to generate the phase-delayed clock signal having a later phase than the phase of the clock signal by the first delay amount indicated by the digital information. The sampling signal generation circuit may include a second digital-controlled delay circuit configured to generate the sampling signal having a later phase than the phase of the clock signal by the second delay amount in accordance with the shift amount and the first delay amount indicated by the digital information.

According to a tenth aspect of the present invention, in the first aspect, the binary circuit may include a comparator, a resistor, a switch, and a condenser. The comparator includes a first terminal to which the video signal is input and a second terminal and is configured to generate the binary signal on the basis of a result of comparing a voltage of the first terminal with a voltage of the second terminal. The video signal is input into the resistor. The switch includes a third terminal and a fourth terminal and is configured to go into any one of an ON state and an OFF state. The video signal output from the resistor is input into the third terminal. The fourth terminal is electrically connected to the second terminal. The third terminal and the fourth terminal are electrically connected to each other in the ON state. The third terminal and the fourth terminal are electrically insulated from each other in the OFF state. The condenser is electrically connected to the second terminal and the fourth terminal. After a state of the switch changes to the ON state, the switch is configured to go into the OFF state. When the state of the switch is the OFF state, the comparator is configured to generate the binary signal.

According to an eleventh aspect of the present invention, in the tenth aspect, the binary circuit may further include a differentiation-amplification circuit configured to perform differentiation and amplification on the video signal. The video signal may be input into the resistor and the differentiation-amplification circuit. The video signal on which the differentiation and the amplification are performed may be output from the differentiation-amplification circuit and may be input into the first terminal.

According to a twelfth aspect of the present invention, an endoscope system includes a scope, a video-signal-capturing circuit, and the phase adjustment circuit. The scope includes an image sensor. The image sensor is disposed in a distal end of the scope and is configured to generate the video signal. The scope and the video-signal-capturing circuit are connected to each other by a signal line configured to transfer the video signal output from the image sensor. The video-signal-capturing circuit is configured to capture the video signal on the basis of the sampling signal.

DETAILED DESCRIPTION OF THE INVENTION

Hereinafter, embodiments of the present invention will be described with reference to the drawings.

First Embodiment

Figure 1:
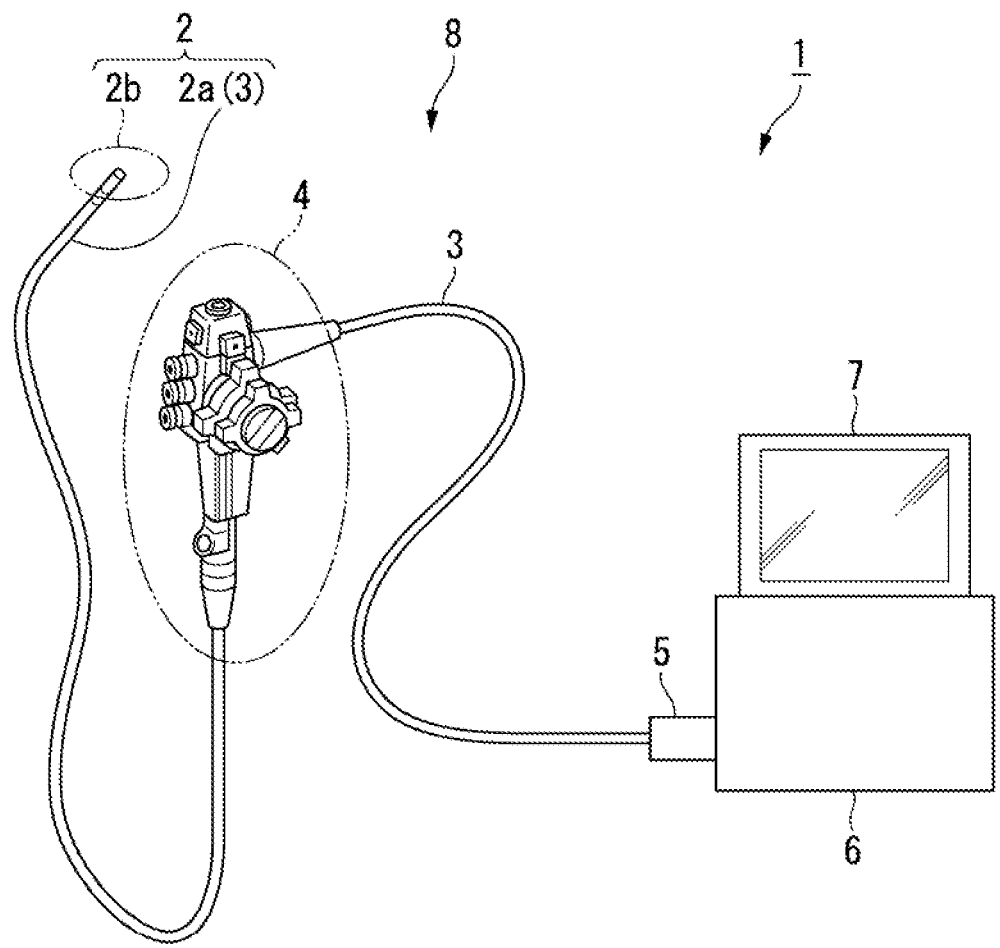
FIG. 1 is a schematic diagram showing a configuration of an endoscope system according to a first embodiment of the present invention.

FIG. 1 shows a configuration of an endoscope system 1 according to a first embodiment of the present invention. The endoscope system 1 shown in FIG. 1 includes an endoscope insertion unit 2, a transmission cable 3, an operation unit 4, a connector unit 5, a processor 6, and a display device 7. The endoscope insertion unit 2, the transmission cable 3, the operation unit 4, and the connector unit 5 constitute a scope 8.

Figure 2:
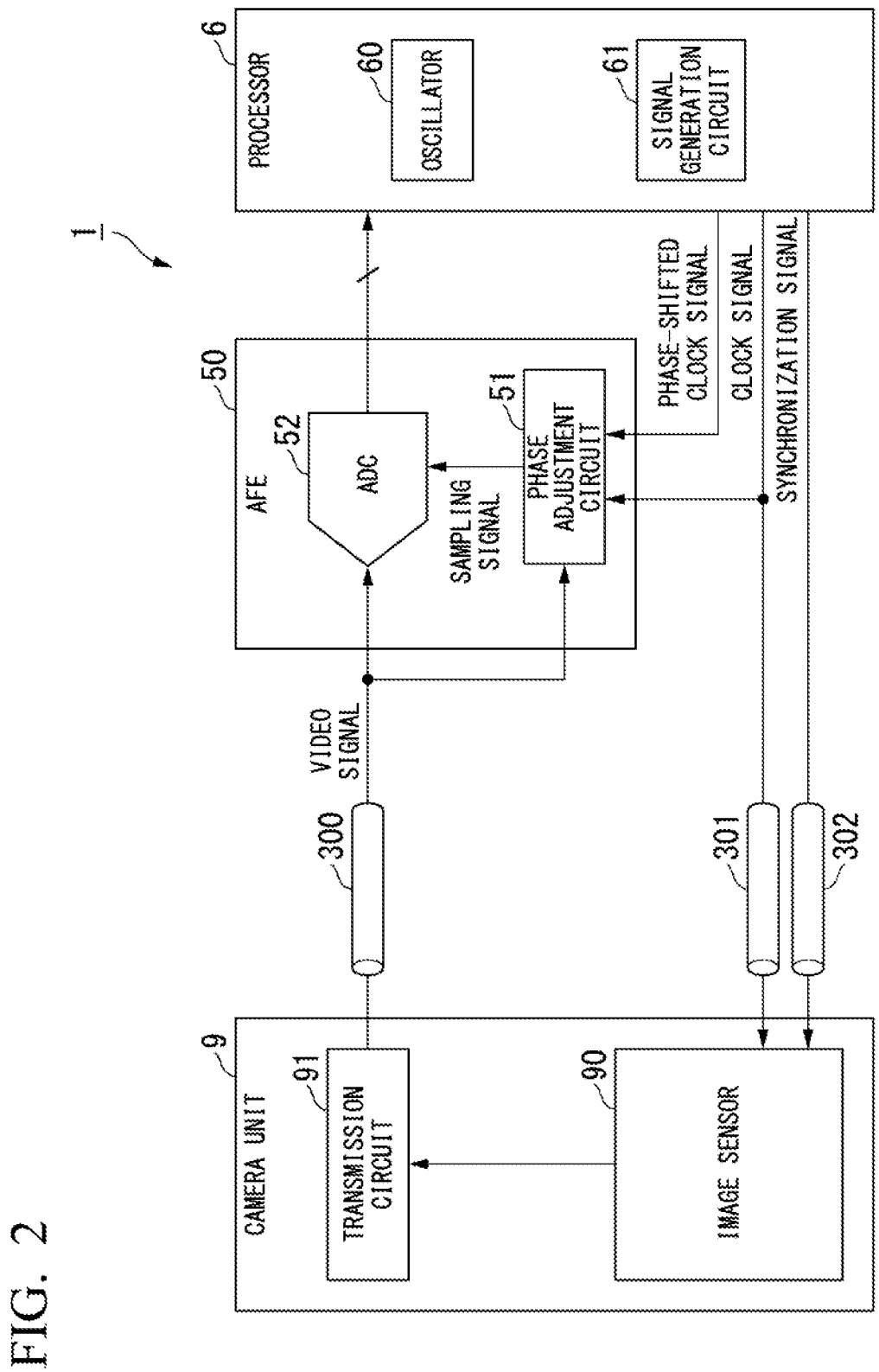
FIG. 2 is a block diagram showing a configuration of the endoscope system according to the first embodiment of the present invention.

The endoscope insertion unit 2 includes an insertion unit 2a. The insertion unit 2a is part of the transmission cable 3. The insertion unit 2a is to be inserted inside a subject. The endoscope insertion unit 2 generates a video signal (image data) by imaging the inside of the subject. The endoscope insertion unit 2 outputs the generated video signal to the processor 6. A camera unit 9 shown in FIG. 2 is disposed in a distal end 2b of the insertion unit 2a. In the insertion unit 2a, the operation unit 4 is connected to the end part opposite the distal end 2b. The operation unit 4 accepts various operations for the endoscope insertion unit 2 from a user.

The transmission cable 3 connects the camera unit 9 and the connector unit 5 together. The video signal generated by the camera unit 9 is output to the connector unit 5 via the transmission cable 3.

The connector unit 5 is connected to the endoscope insertion unit 2 and the processor 6. The connector unit 5 performs predetermined processing on the video signal output from the endoscope insertion unit 2. The connector unit 5 outputs the video signal to the processor 6.

The processor 6 performs image processing on the video signal output from the connector unit 5. Furthermore, the processor 6 centrally controls the entire endoscope system 1.

The display device 7 displays a video on the basis of the video signal processed by the processor 6. In addition, the display device 7 displays various kinds of information related to the endoscope system 1.

The endoscope system 1 includes a light source device that generates illumination light emitted to the subject. The light source device is not shown in FIG. 1.

FIG. 2 shows an internal configuration of the endoscope system 1. The endoscope system 1 shown in FIG. 2 includes the camera unit 9, an AFE 50, and the processor 6. The camera unit 9 is disposed in the distal end 2b of the scope 8. The AFE 50 is included in the connector unit 5. The operation unit 4 and the display device 7 are not shown in FIG. 2.

The camera unit 9 generates the video signal and transmits the video signal to the AFE 50. The camera unit 9 includes an image sensor 90 and a transmission circuit 91. The AFE 50 captures the video signal transmitted by the camera unit 9 and performs signal processing on the video signal. The AFE 50 includes a phase adjustment circuit 51 and an ADC 52 (video-signal-capturing circuit). The processor 6 generates a necessary signal for an operation of each of the camera unit 9 and the AFE 50. The processor 6 includes an oscillator 60 and a signal generation circuit 61.

At least one of the phase adjustment circuit 51 and the ADC 52 may be disposed in the operation unit 4 or the processor 6. At least one of the oscillator 60 and the signal generation circuit 61 may be disposed in the operation unit 4 or the connector unit 5.

The camera unit 9 and the AFE 50 are connected to each other by a cable 300. The camera unit 9 and the processor 6 are connected to each other by a cable 301 and a cable 302. Each cable includes a signal line and is disposed in the transmission cable 3.

A schematic configuration of the endoscope system 1 will be described. The image sensor 90 is disposed in the distal end 2b of the camera unit 9 and generates the video signal. The scope 8 and the ADC 52 are connected to each other by the cable 300 (signal line) that transfers the video signal output from the image sensor 90. The phase adjustment circuit 51 generates a sampling signal. The ADC 52 captures the video signal on the basis of the sampling signal.

A detailed configuration of the endoscope system 1 will be described. The image sensor 90 includes a plurality of pixels disposed in a matrix shape. The image sensor 90 performs imaging in accordance with a clock signal and a synchronization signal output from the processor 6 and outputs an analog video signal to the transmission circuit 91. The transmission circuit 91 transmits the video signal to the AFE 50. The video signal is transferred to the AFE 50 by the cable 300.

The oscillator 60 generates the clock signal. The signal generation circuit 61 generates the synchronization signal and a phase-shifted clock signal on the basis of the clock signal. The synchronization signal includes a vertical synchronization signal and a horizontal synchronization signal. The phase of the phase-shifted clock signal is different from that of the clock signal. The processor 6 outputs the clock signal and the phase-shifted clock signal to the phase adjustment circuit 51 and transmits the clock signal and the synchronization signal to the camera unit 9. The clock signal is transferred to the camera unit 9 by the cable 301. The synchronization signal is transferred to the camera unit 9 by the cable 302.

The phase adjustment circuit 51 generates the sampling signal on the basis of the clock signal and the phase-shifted clock signal and outputs the sampling signal to the ADC 52. The ADC 52 performs AD conversion. The ADC 52 captures the video signal at a timing indicated by the sampling signal and converts the analog video signal into a digital video signal. The ADC 52 outputs the digital video signal to the processor 6.

The ADC 52 functions as a video-signal-capturing circuit. The video-signal-capturing circuit is not limited to the ADC 52. For example, the video-signal-capturing circuit may be a reception circuit that receives the video signal. The video-signal-capturing circuit may be a signal-processing circuit that performs different signal processing from the AD conversion on the video signal.

Figure 3:
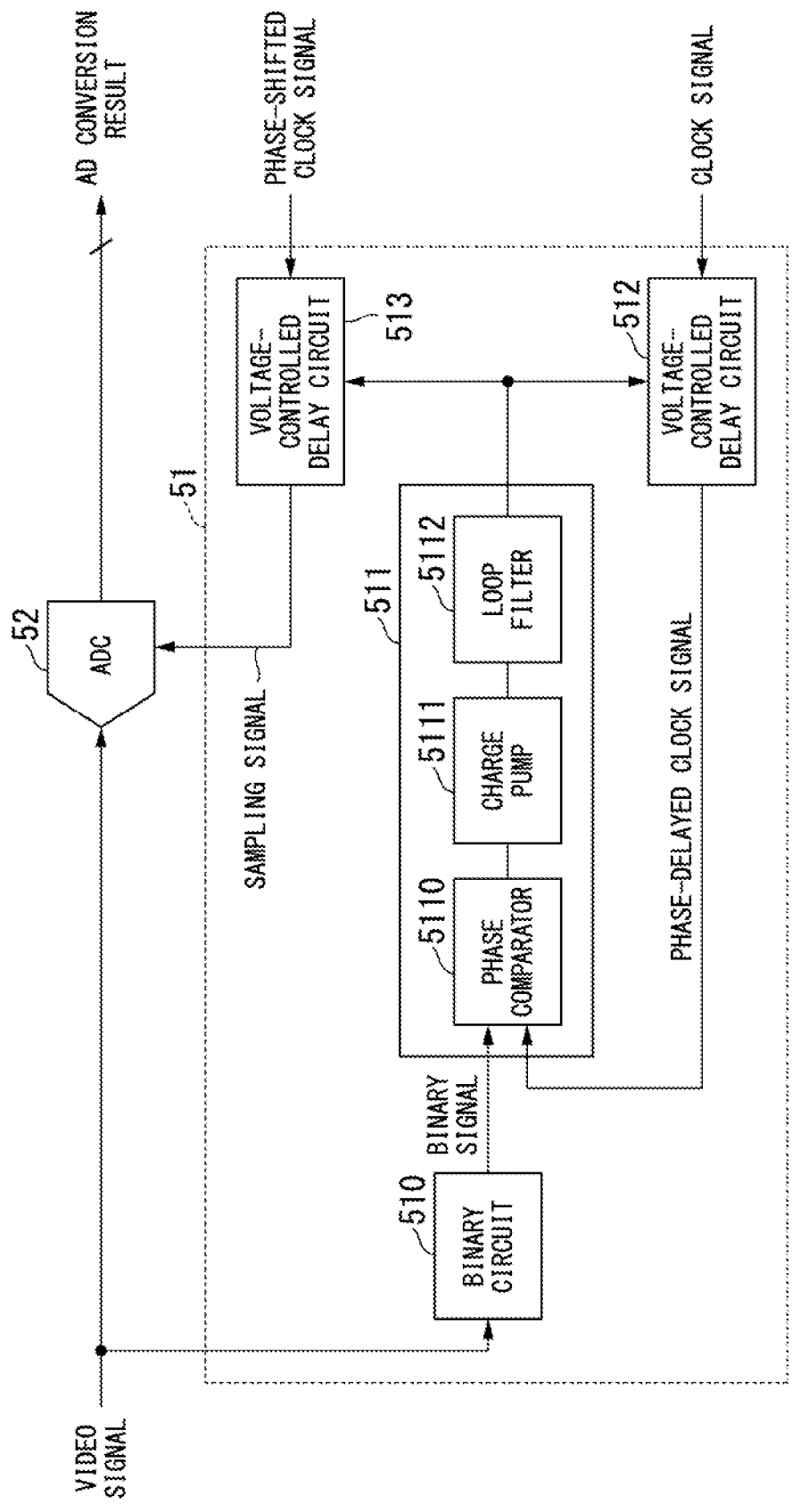
FIG. 3 is a block diagram showing a configuration of a phase adjustment circuit included in the endoscope system according to the first embodiment of the present invention.

FIG. 3 shows a configuration of the phase adjustment circuit 51. The phase adjustment circuit 51 shown in FIG. 3 includes a binary circuit 510, a delay time control circuit 511, a voltage-controlled delay circuit 512 (phase-delayed clock signal generation circuit), and a voltage-controlled delay circuit 513 (sampling signal generation circuit).

A schematic configuration of the phase adjustment circuit 51 will be described. The phase adjustment circuit 51 generates the sampling signal used for capturing the video signal at a later timing than that indicated by the clock signal. The binary circuit 510 detects an edge of the video signal and outputs a binary signal having a voltage that changes at a timing of the detected edge. The voltage-controlled delay circuit 512 generates a phase-delayed clock signal having a later phase than that of the clock signal by a first delay amount. The delay time control circuit 511 causes the phase of the binary signal and the phase of the phase-delayed clock signal to match each other by adjusting the first delay amount on the basis of the binary signal and the phase-delayed clock signal. The voltage-controlled delay circuit 513 generates the sampling signal having a later phase than that of the clock signal by a second delay amount. The second delay amount is in accordance with both a phase shift amount, which is based on a timing indicated by the clock signal, and the first delay amount adjusted by the delay time control circuit 511.

A detailed configuration of the phase adjustment circuit 51 will be described. The video signal is input into the binary circuit 510. The binary circuit 510 detects an edge at which the voltage of the video signal sharply changes and generates the binary signal. The binary signal has a high level or a low level. The voltage of the binary signal changes from the low level to the high level or from the high level to the low level at the timing of the edge. The binary circuit 510 outputs the binary signal to the delay time control circuit 511.

The clock signal is input into the voltage-controlled delay circuit 512. The clock signal has the high level or the low level, and has a predetermined frequency. The voltage-controlled delay circuit 512 generates the phase-delayed clock signal by delaying the phase of the clock signal by the first delay amount. The first delay amount is controlled on the basis of a control voltage input into the voltage-controlled delay circuit 512. The voltage-controlled delay circuit 512 outputs the phase-delayed clock signal to the delay time control circuit 511.

The binary signal and the phase-delayed clock signal are input into the delay time control circuit 511. The delay time control circuit 511 includes a phase comparator 5110, a charge pump 5111, and a loop filter 5112.

The phase comparator 5110 compares the phase of the binary signal with the phase of the phase-delayed clock signal. The phase comparator 5110 outputs a signal in accordance with the difference between the phase of the binary signal and the phase of the phase-delayed clock signal to the charge pump 5111. The charge pump 5111 generates an analog signal used for adjusting a phase of a signal on the basis of the signal output from the phase comparator 5110. The loop filter 5112 generates a control voltage on the basis of the analog signal output from the charge pump 5111 and outputs the control voltage to the voltage-controlled delay circuit 512 and the voltage-controlled delay circuit 513.

The voltage-controlled delay circuit 512 generates the phase-delayed clock signal by giving the first delay amount adjusted on the basis of the control signal to the clock signal. Consequently, the phase of the binary signal and the phase of the phase-delayed clock signal match each other.

The phase-shifted clock signal is input into the voltage-controlled delay circuit 513. The voltage-controlled delay circuit 513 generates the sampling signal by delaying the phase of the phase-shifted clock signal by the first delay amount. The first delay amount is controlled on the basis of a control voltage input into the voltage-controlled delay circuit 513. The voltage-controlled delay circuit 513 includes the same configuration as that of the voltage-controlled delay circuit 512. Therefore, the first delay amount given to the phase-shifted clock signal by the voltage-controlled delay circuit 513 is the same as that given to the clock signal by the voltage-controlled delay circuit 512. The voltage-controlled delay circuit 513 outputs the sampling signal to the ADC 52.

The sampling signal is input into the ADC 52. The ADC 52 performs AD conversion on the video signal at a timing indicated by the sampling signal. The ADC 52 outputs the digital video signal as an AD conversion result to the processor 6.

While the video signal passes through the cable 300, the waveform of the video signal deteriorates. Therefore, it is difficult to compare the phase of the video signal with the phase of the phase-delayed clock signal. The binary circuit 510 generates the binary signal having clear edges. The delay time control circuit 511 can easily cause the phase of the binary signal and the phase of the phase-delayed clock signal to match each other by using the binary signal instead of using the video signal having a deteriorated waveform.

In general, the amplitude of the video signal is considerably smaller than those of the clock signal and the phase-delayed clock signal. The binary circuit 510 generates the binary signal having almost the same amplitude as that of the phase-delayed clock signal. The delay time control circuit 511 can easily cause the phase of the binary signal and the phase of the phase-delayed clock signal to match each other by using the binary signal instead of using the video signal having a small amplitude.

The difference between the phase of the clock signal and the phase of the phase-shifted clock signal is a predetermined shift amount. The predetermined shift amount is set in advance such that the timing indicated by the sampling signal is included in a period during which the voltage of the video signal is stable. The difference between the phase of the phase-shifted clock signal and the phase of the sampling signal is the first delay amount. The phase of the sampling signal is later than that of the clock signal by the second delay amount. The second delay amount is the difference between the first delay amount and the predetermined shift amount. The predetermined shift amount is less than the first delay amount. The second delay amount is less than the first delay amount.

Figure 4:
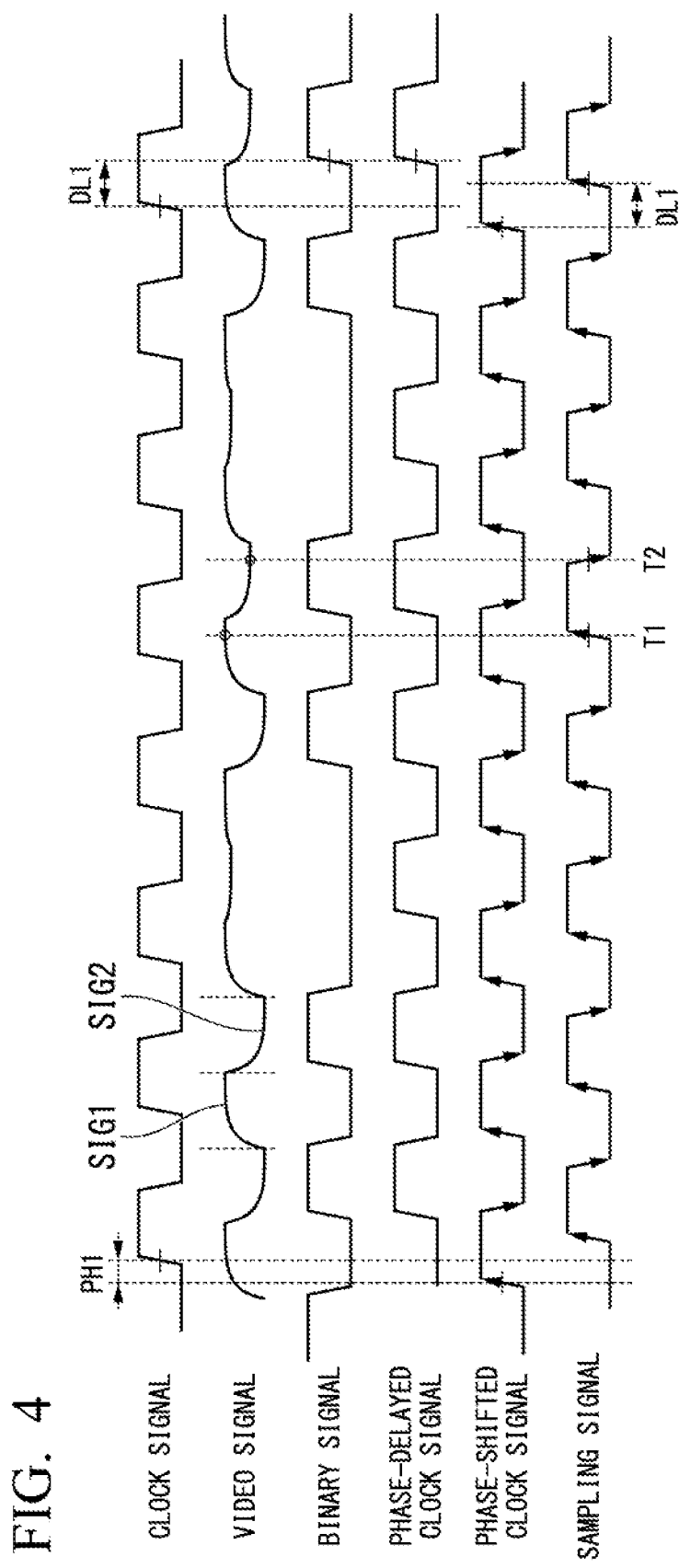
FIG. 4 is a timing chart showing waveforms of signals in the endoscope system according to the first embodiment of the present invention.

FIG. 4 shows waveforms of the clock signal, the video signal, the binary signal, the phase-delayed clock signal, the phase-shifted clock signal, and the sampling signal. The horizontal direction in FIG. 4 indicates time, and the vertical direction in FIG. 4 indicates a voltage of each signal.

The video signal includes a standard signal SIG1 (first signal) having a predetermined voltage and a pixel signal SIG2 (second signal) having a voltage that fluctuates. The standard signal SIG1 has the predetermined voltage, and the pixel signal SIG2 has a voltage in accordance with the amount of light incident on the plurality of pixels. The standard signal SIG1 and the pixel signal SIG2 appear one after the other. Since the delay time control circuit 511 adjusts the first delay amount, the phase of the binary signal and the phase of the phase-delayed clock signal match each other. The phase of the binary signal and the phase of the phase-delayed clock signal are later than that of the clock signal by a delay amount DL1. The delay amount DL1 corresponds to the first delay amount.

The phase of the phase-shifted clock signal is ahead of that of the clock signal by a shift amount PH1. In other words, the phase of the phase-shifted clock signal is later than that of the clock signal by (360−PH1) degrees. The shift amount PH1 corresponds to a phase shift amount that is based on a timing indicated by the clock signal. The phase of the sampling signal is later than that of the phase-shifted clock signal by the delay amount DL1. The phase of the sampling signal is later than that of the clock signal by the difference (second delay amount) between the delay amount DL1 and the shift amount PH1. The ADC 52 captures the standard signal SIG1 at a timing T1 at which the sampling signal rises and captures the pixel signal SIG2 at a timing T2 at which the sampling signal falls.

The first delay amount used for setting the second delay amount is set on the basis of a timing at which the voltage of the video signal changes. Therefore, the phase adjustment circuit 51 can set the phase of the sampling signal on the basis of the timing at which the voltage of the video signal changes. The ADC 52 can capture the video signal at a stable timing regardless of the delay time of the video signal. The phase adjustment circuit 51 can reduce the load for adjusting the phase of the sampling signal.

Second Embodiment

Figure 5:
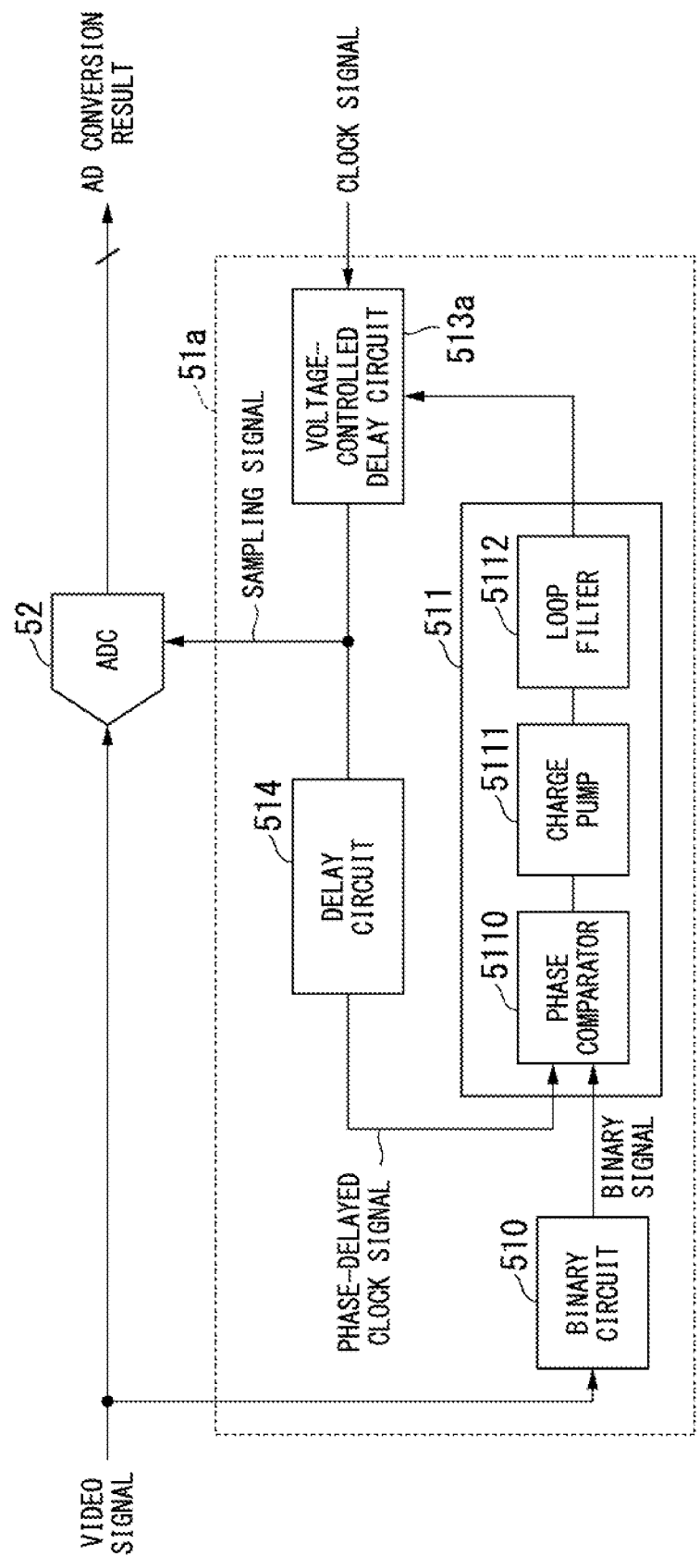
FIG. 5 is a block diagram showing a configuration of a phase adjustment circuit included in an endoscope system according to a second embodiment of the present invention.

FIG. 5 shows a configuration of a phase adjustment circuit 51a according to a second embodiment of the present invention. The phase adjustment circuit 51a shown in FIG. 5 includes a binary circuit 510, a delay time control circuit 511, a voltage-controlled delay circuit 513a (sampling signal generation circuit), and a delay circuit 514 (phase-delayed clock signal generation circuit). The same configuration as that shown in FIG. 3 will not be described.

A schematic configuration of the phase adjustment circuit 51a will be described. The voltage-controlled delay circuit 513a receives the clock signal and generates a sampling signal by adding a second delay amount to the clock signal. The delay circuit 514 receives the sampling signal generated by the voltage-controlled delay circuit 513a and generates a phase-delayed clock signal by changing the phase of the sampling signal by a predetermined shift amount.

A detailed configuration of the phase adjustment circuit 51a will be described. The clock signal is input into the voltage-controlled delay circuit 513a. The voltage-controlled delay circuit 513a generates the sampling signal by delaying the phase of the clock signal by the second delay amount. The second delay amount is the difference between a first delay amount and the predetermined shift amount. The predetermined shift amount is less than the first delay amount. The second delay amount is less than the first delay amount. The first delay amount is controlled on the basis of a control voltage input into the voltage-controlled delay circuit 513a. The phase of the sampling signal is later than that of the clock signal by the second delay amount. The voltage-controlled delay circuit 513a outputs the sampling signal to the ADC 52 and the delay circuit 514.

The sampling signal is input into the delay circuit 514. The delay circuit 514 generates the phase-delayed clock signal by delaying the phase of the sampling signal by the predetermined shift amount. The phase of the phase-delayed clock signal is later than that of the sampling signal by the predetermined shift amount. The phase of the phase-delayed clock signal is later than that of the clock signal by the first delay amount. The delay circuit 514 outputs the phase-delayed clock signal to the delay time control circuit 511.

In the phase adjustment circuit 51 shown in FIG. 3, the voltage-controlled delay circuit 512 and the voltage-controlled delay circuit 513 include the same configuration in design. However, there is a possibility that the first delay amount given by the voltage-controlled delay circuit 512 and the first delay amount given by the voltage-controlled delay circuit 513 are not the same due to the influence of deviations of conditions or the like of the production process. Therefore, there is a possibility that the phase of the sampling signal is not an intended phase when the phase of the binary signal and the phase of the phase-delayed clock signal match each other.

The phase adjustment circuit 51a does not include the voltage-controlled delay circuit 512 shown in FIG. 3, and the phase-delayed clock signal is generated on the basis of the sampling signal generated by the voltage-controlled delay circuit 513a. Therefore, the phase adjustment circuit 51a can generate the sampling signal having an accurate phase.

(Modified Example of Second Embodiment)

Figure 6:
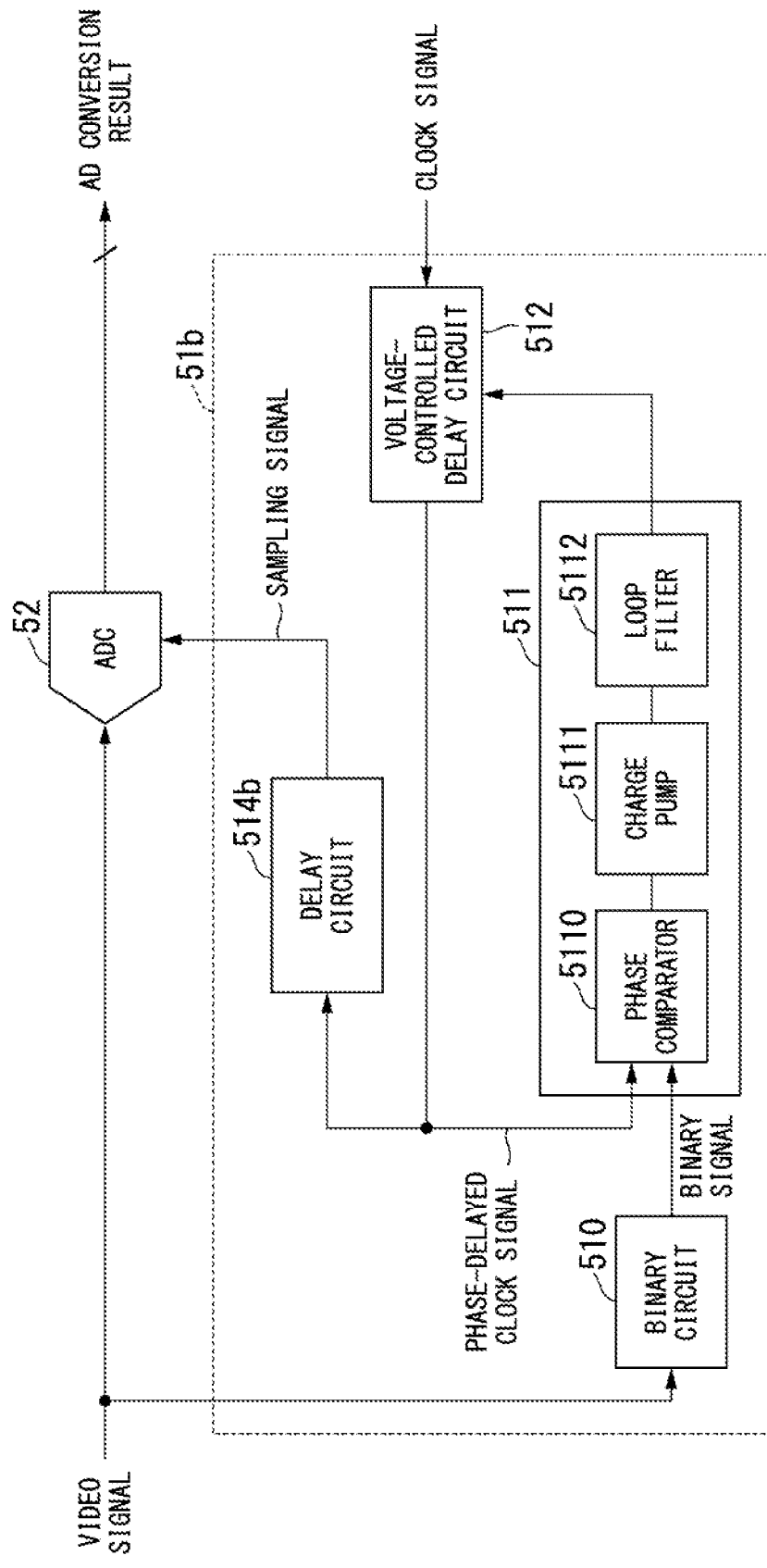
FIG. 6 is a block diagram showing a configuration of a phase adjustment circuit included in an endoscope system according to a modified example of the second embodiment of the present invention.

FIG. 6 shows a configuration of a phase adjustment circuit 51b according to a modified example of the second embodiment of the present invention. The phase adjustment circuit 51b shown in FIG. 6 includes a binary circuit 510, a delay time control circuit 511, a voltage-controlled delay circuit 512 (phase-delayed clock signal generation circuit), and a delay circuit 514b (sampling signal generation circuit). The same configuration as that shown in FIG. 3 will not be described.

A schematic configuration of the phase adjustment circuit 51b will be described. The voltage-controlled delay circuit 512 receives the clock signal and generates a phase-delayed clock signal by adding a first delay amount to the clock signal. The delay circuit 514b receives the phase-delayed clock signal generated by the voltage-controlled delay circuit 512 and generates a sampling signal by changing the phase of the phase-delayed clock signal by a predetermined shift amount.

A detailed configuration of the phase adjustment circuit 51b will be described. The voltage-controlled delay circuit 512 is the same as that shown in FIG. 3. The voltage-controlled delay circuit 512 outputs the phase-delayed clock signal to the delay time control circuit 511 and the delay circuit 514b. The phase-delayed clock signal is input into the delay circuit 514b. The delay circuit 514b generates the sampling signal by advancing the phase of the phase-delayed clock signal by the predetermined shift amount.

The phase of the phase-delayed clock signal is later than that of the clock signal by the first delay amount. The phase of the sampling signal is ahead of that of the phase-delayed clock signal by the predetermined shift amount. The phase of the sampling signal is later than that of the clock signal by a second delay amount. The second delay amount is the difference between the first delay amount and the predetermined shift amount. The predetermined shift amount is less than the first delay amount. The second delay amount is less than the first delay amount.

The phase adjustment circuit 51b does not include the voltage-controlled delay circuit 512 shown in FIG. 3, and the sampling signal is generated on the basis of the phase-delayed clock signal generated by the voltage-controlled delay circuit 513a. Therefore, the phase adjustment circuit 51b can generate the sampling signal having an accurate phase.

Third Embodiment

Figure 7:
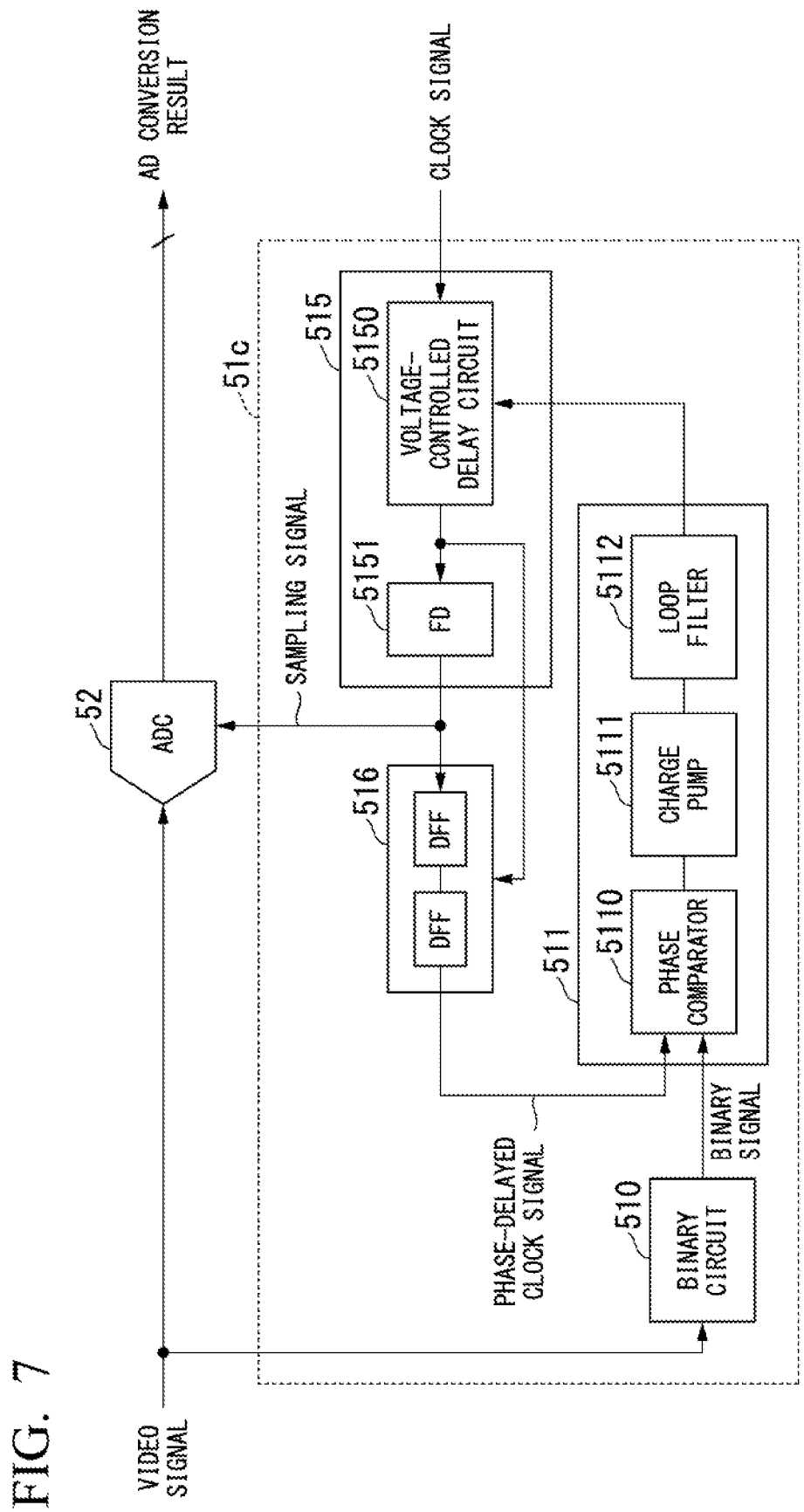
FIG. 7 is a block diagram showing a configuration of a phase adjustment circuit included in an endoscope system according to a third embodiment of the present invention.

FIG. 7 shows a configuration of a phase adjustment circuit 51c according to a third embodiment of the present invention. The phase adjustment circuit 51c shown in FIG. 7 includes a binary circuit 510, a delay time control circuit 511, a sampling signal generation circuit 515, and a delay circuit 516 (phase-delayed clock signal generation circuit). The same configuration as that shown in FIG. 3 will not be described.

A schematic configuration of the phase adjustment circuit 51c will be described. The sampling signal generation circuit 515 receives a clock signal having a higher frequency than that of the video signal. The sampling signal generation circuit 515 generates a sampling signal having almost the same frequency as that of the video signal by adding a second delay amount to the clock signal and by dividing or reducing the frequency of the clock signal. The delay circuit 516 receives the sampling signal generated by the sampling signal generation circuit 515 and generates a phase-delayed clock signal by changing the phase of the sampling signal by a predetermined shift amount by using a shift register.

A detailed configuration of the phase adjustment circuit 51c will be described. The sampling signal generation circuit 515 includes a voltage-controlled delay circuit 5150 and a frequency divider 5151. The signal generation circuit 61 of the processor 6 generates a fast clock signal having a higher frequency than that of the video signal. The clock signal is input into the voltage-controlled delay circuit 5150.

The voltage-controlled delay circuit 5150 delays the phase of the clock signal by the second delay amount. The second delay amount is the difference between a first delay amount and the predetermined shift amount. The predetermined shift amount is less than the first delay amount. The second delay amount is less than the first delay amount. The first delay amount is controlled on the basis of a control voltage input from the delay time control circuit 511 into the voltage-controlled delay circuit 5150. The phase of the clock signal generated by the voltage-controlled delay circuit 5150 is later than that of the clock signal generated by the signal generation circuit 61 by the second delay amount. The voltage-controlled delay circuit 5150 outputs the generated clock signal to the frequency divider 5151 and the delay circuit 516.

The clock signal generated by the voltage-controlled delay circuit 5150 is input into the frequency divider 5151. The frequency divider 5151 generates the sampling signal by dividing or reducing the frequency of the clock signal. The frequency of the sampling signal is almost the same as that of the video signal. For example, the frequency of the clock signal is an integer times as great as that of the sampling signal. The integer is two or more. The phase of the sampling signal is later than that of the clock signal by the second delay amount. The frequency divider 5151 outputs the sampling signal to the ADC 52 and the delay circuit 516.

Figure 8:
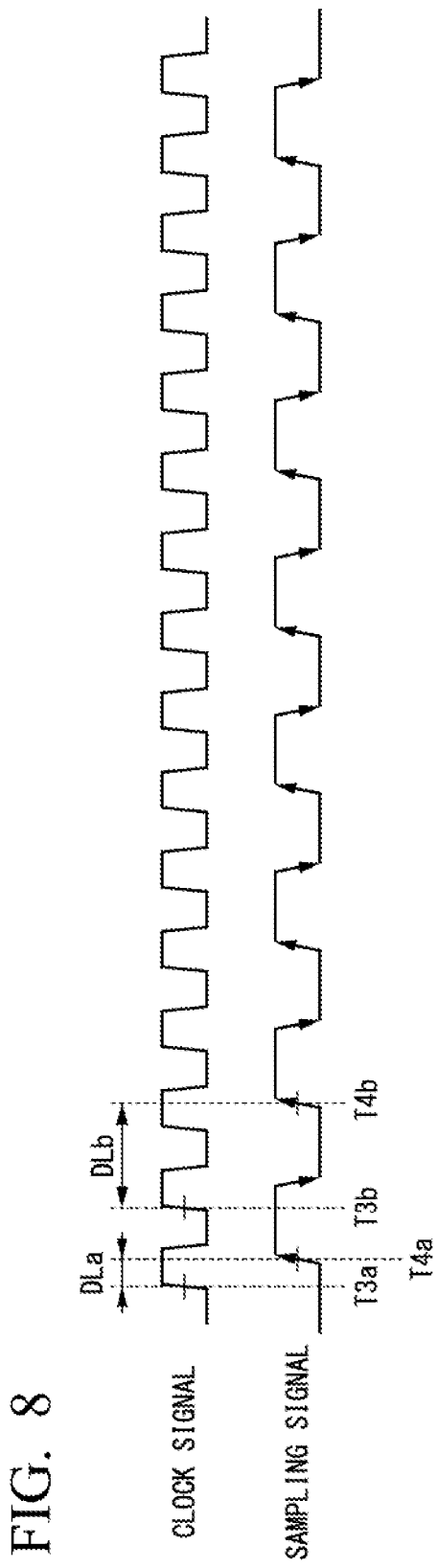
FIG. 8 is a timing chart showing waveforms of signals in the endoscope system according to the third embodiment of the present invention.

FIG. 8 shows waveforms of the clock signal generated by the voltage-controlled delay circuit 5150 and the sampling signal. The horizontal direction in FIG. 8 indicates time, and the vertical direction in FIG. 8 indicates a voltage of each signal. In FIG. 8, an example in which the frequency of the clock signal is twice as great as that of the sampling signal is shown.

For example, the delay amount of the sampling signal is defined as the minimum value of the difference between a timing at which the clock signal rises and a timing at which the sampling signal rises. A delay amount DLa shown in FIG. 8 is the difference between a timing T3a at which the clock signal rises and a timing T4a at which the sampling signal rises. The timing T4a is a timing at which the sampling signal rises after the timing T3a and closest to the timing T3a. A delay amount DLb shown in FIG. 8 is the difference between a timing T3b at which the clock signal rises and a timing T4b at which the sampling signal rises. The timing T4b is a timing at which the sampling signal rises after the timing T3b and closest to the timing T3b. The delay amount DLa is less than the delay amount DLb. The delay amount of the sampling signal is defined as the delay amount DLa.

In the above-described example, a delay amount of a signal is defined on the basis of a timing at which each signal rises. The delay amount of the signal may be defined on the basis of a timing at which each signal falls.

The delay circuit 516 is a shift register. For example, the delay circuit 516 includes one or more D-type flip-flop circuits. In a case in which the delay circuit 516 includes two or more D-type flip-flop circuits, the two or more D-type flip-flop circuits are connected in series.

The sampling signal is input into the delay circuit 516. The delay circuit 516 generates the phase-delayed clock signal by delaying the phase of the sampling signal by the predetermined shift amount. The phase of the phase-delayed clock signal is later than that of the sampling signal by the predetermined shift amount. The phase of the phase-delayed clock signal is later than that of the clock signal generated by the signal generation circuit 61 by the first delay amount. The delay circuit 516 outputs the phase-delayed clock signal to the delay time control circuit 511.

Each D-type flip-flop circuit included in the delay circuit 516 changes the phase of the sampling signal by the length of the cycle of the clock signal. The shift amount in the delay circuit 516 is controlled by units of the cycle of the clock signal. Therefore, the phase adjustment circuit 51c can generate the sampling signal having an accurate phase independently of process, voltage, and temperature (PVT).

Fourth Embodiment

Figure 9:
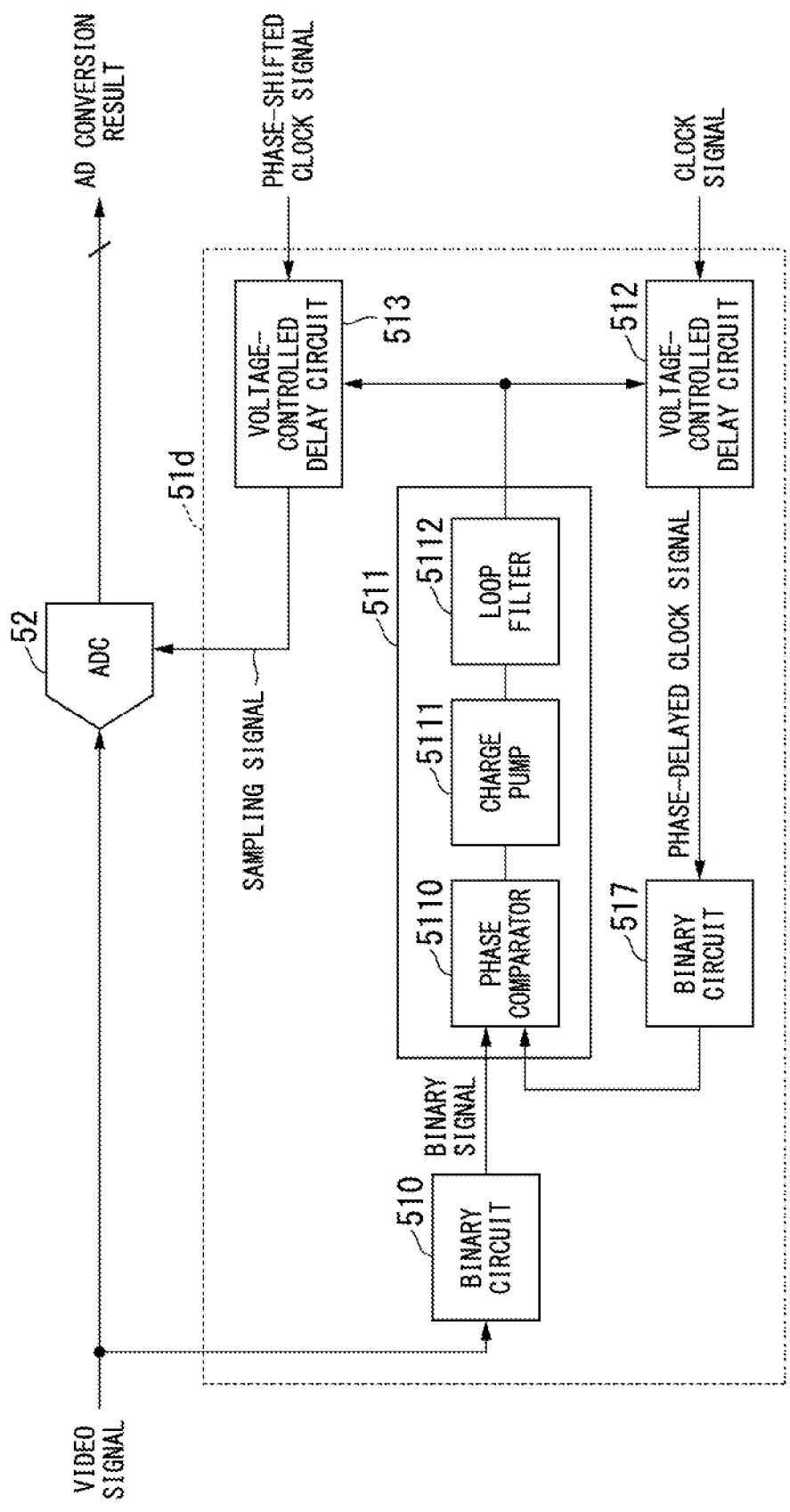
FIG. 9 is a block diagram showing a configuration of a phase adjustment circuit included in an endoscope system according to a fourth embodiment of the present invention.

FIG. 9 shows a configuration of a phase adjustment circuit 51d according to a fourth embodiment of the present invention. The phase adjustment circuit 51*d* shown in FIG. 9 includes a binary circuit 510, a delay time control circuit 511, a voltage-controlled delay circuit 512 (phase-delayed clock signal generation circuit), a voltage-controlled delay circuit 513 (sampling signal generation circuit), and a binary circuit 517 (delay circuit). The same configuration as that shown in FIG. 3 will not be described.

A schematic configuration of the phase adjustment circuit 51*d* will be described. The binary circuit 517 receives a phase-delayed clock signal generated by the voltage-controlled delay circuit 512. The binary circuit 517 adds a third delay amount to the phase-delayed clock signal and outputs the phase-delayed clock signal to which the third delay amount has been added to the delay time control circuit 511. The third delay amount is the difference between the phase of the video signal input into the binary circuit 510 and the phase of the binary signal generated by the binary circuit 510.

A detailed configuration of the phase adjustment circuit 51*d* will be described. The phase-delayed clock signal is input into the binary circuit 517. The binary circuit 517 detects an edge at which the voltage of the phase-delayed clock signal sharply changes and generates a binarized phase-delayed clock signal (binary signal). The phase-delayed clock signal has a high level or a low level. The binary circuit 517 outputs the phase-delayed clock signal to the delay time control circuit 511.

The binary circuit 517 includes the same configuration as that of the binary circuit 510. Therefore, the delay amount given to the phase-delayed clock signal by the binary circuit 517 is the same as the third delay amount given to the video signal by the binary circuit 510.

In the phase adjustment circuit 51 shown in FIG. 3, the phase of the video signal and the phase of the binary signal generated by the binary circuit 510 are different from each other by the third delay amount. Therefore, the phase of the sampling signal may be later than that that is based on the video signal by the third delay amount when the phase of the binary signal and the phase of the phase-delayed clock signal match each other.

In the phase adjustment circuit 51*d* shown in FIG. 9, the binary circuit 517 gives the phase-delayed clock signal the same delay amount as the third delay amount given by the binary circuit 510 to the video signal. Therefore, the phase adjustment circuit 51*d* can generate the sampling signal having an accurate phase that is based on the video signal.

The phase adjustment circuit 51*a* shown in FIG. 5 may include the binary circuit 517 that adds the third delay amount to the phase-delayed clock signal output from the delay circuit 514. The phase adjustment circuit 51*b* shown in FIG. 6 may include the binary circuit 517 that adds the third delay amount to the phase-delayed clock signal output from the voltage-controlled delay circuit 512. The phase adjustment circuit 51*c* shown in FIG. 7 may include the binary circuit 517 that adds the third delay amount to the phase-delayed clock signal output from the delay circuit 516.

(Modified Example of Fourth Embodiment)

Figure 10:
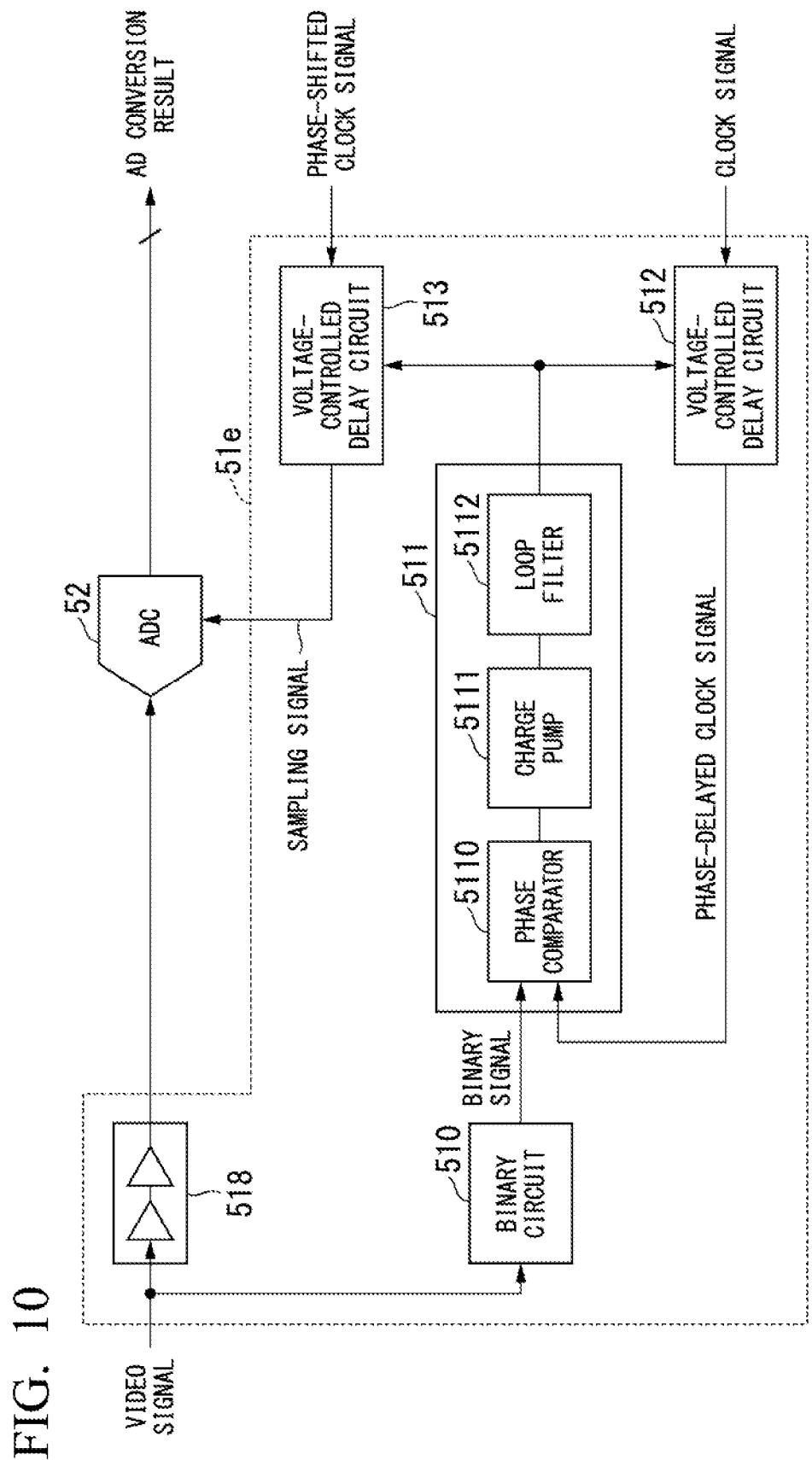
FIG. 10 is a block diagram showing a configuration of a phase adjustment circuit included in an endoscope system according to a modified example of the fourth embodiment of the present invention.

FIG. 10 shows a configuration of a phase adjustment circuit 51*e* according to a modified example of the fourth embodiment of the present invention. The phase adjustment circuit 51*e* shown in FIG. 10 includes a binary circuit 510, a delay time control circuit 511, a voltage-controlled delay circuit 512 (phase-delayed clock signal generation circuit), a voltage-controlled delay circuit 513 (sampling signal generation circuit), and a delay circuit 518. The same configuration as that shown in FIG. 3 will not be described.

A schematic configuration of the phase adjustment circuit 51*e* will be described. The voltage-controlled delay circuit 513 outputs the sampling signal to the ADC 52. The delay circuit 518 adds a third delay amount to the video signal. The third delay amount is the difference between the phase of the video signal input into the binary circuit 510 and the phase of the binary signal. The delay circuit 518 outputs the video signal to which the third delay amount has been added to the ADC 52.

A detailed configuration of the phase adjustment circuit Me will be described. The delay circuit 518 is disposed between the image sensor 90 and the ADC 52 on a transfer path of the video signal. The video signal is input into the delay circuit 518. The delay circuit 518 delays the phase of the video signal by the third delay amount. The delay amount given to the video signal by the delay circuit 518 is the same as the third delay amount given to the video signal by the binary circuit 510. The delay circuit 518 outputs the video signal to which the third delay amount has been added to the ADC 52.

The delay circuit 518 gives the video signal the same delay amount as the third delay amount given to the video signal by the binary circuit 510. Therefore, the phase adjustment circuit 51*e* can generate the sampling signal having an accurate phase that is based on the video signal.

The phase adjustment circuit 51*a* shown in FIG. 5, the phase adjustment circuit 51*b* shown in FIG. 6, or the phase adjustment circuit 51*c* shown in FIG. 7 may include the delay circuit 518.

Fifth Embodiment

Figure 11:
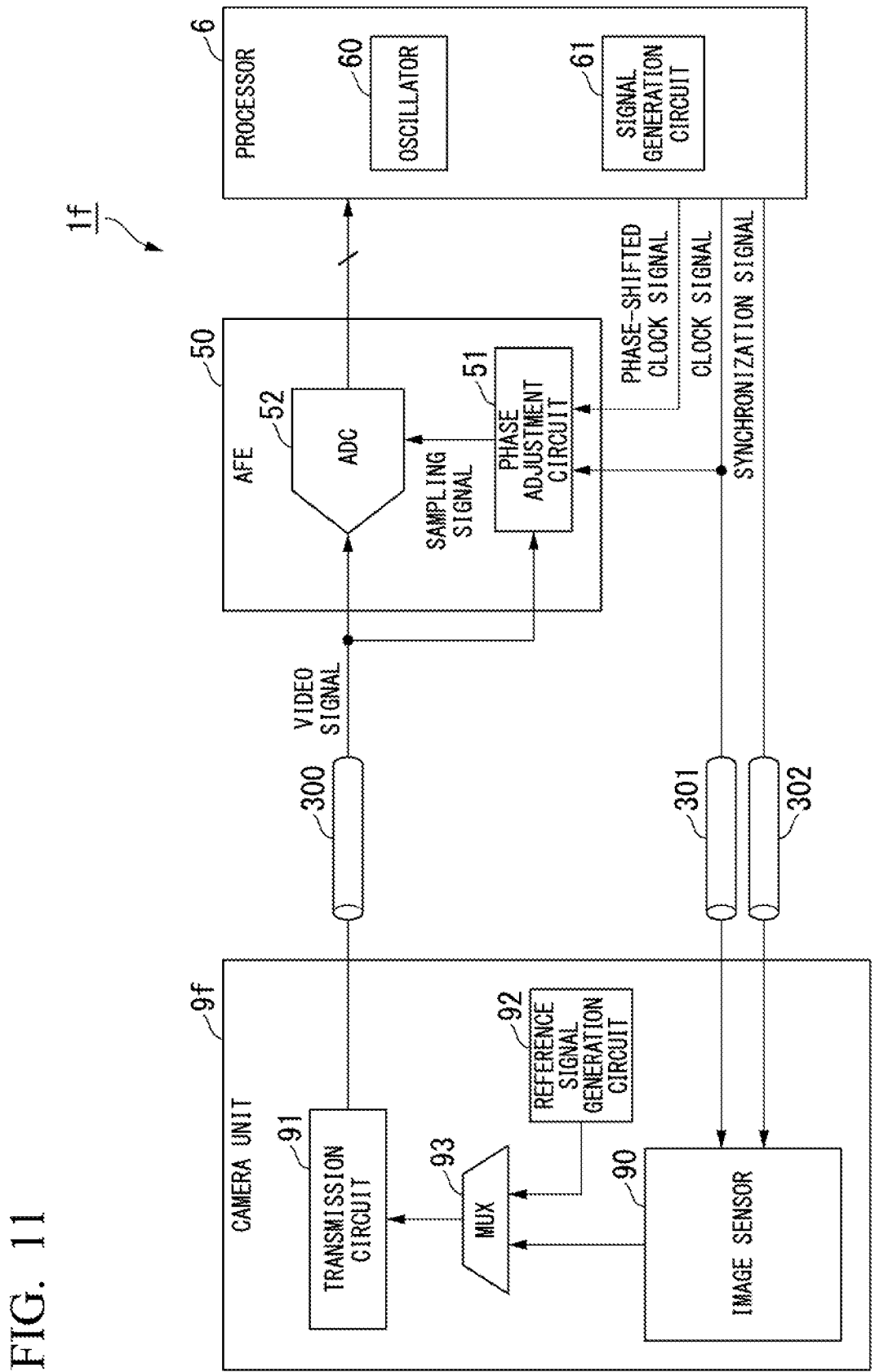
FIG. 11 is a block diagram showing a configuration of an endoscope system according to a fifth embodiment of the present invention.

FIG. 11 shows an internal configuration of an endoscope system 1*f* according to a fifth embodiment of the present invention. The endoscope system 1*f* shown in FIG. 11 includes a camera unit 9*f*, an AFE 50, and a processor 6. The same configuration as that shown in FIG. 2 will not be described.

The camera unit 9 shown in FIG. 2 is changed to the camera unit 9*f*. The camera unit 9*f* includes an image sensor 90, a transmission circuit 91, a reference signal generation circuit 92, and a multiplexer 93.

The image sensor 90 outputs an effective video signal to the multiplexer 93 in an effective period. The effective video signal includes a standard signal having a predetermined voltage and a pixel signal having a voltage that fluctuates. The standard signal has the predetermined voltage, and the pixel signal has a voltage in accordance with the amount of light incident on the plurality of pixels. The standard signal and the pixel signal appear one after the other.

The reference signal generation circuit 92 generates a reference signal in a horizontal blanking period different from the effective period. The horizontal blanking period occurs between an output period (effective period) of the effective video signal generated in pixels in one row and an output period (effective period) of the effective video signal generated in pixels in the next row. The effective period and the horizontal blanking period appear one after the other. The reference signal has one of two different predetermined voltages. The reference signal generation circuit 92 outputs the reference signal to the multiplexer 93.

The reference signal has a first voltage or a second voltage. For example, the first voltage is the same as the voltage of the standard signal. The first voltage may be the high level. The second voltage is greater than or equal to the minimum voltage of the pixel signal and is less than the maximum voltage of the pixel signal. The minimum voltage of the pixel signal corresponds to the maximum amount of electric charge generated in the plurality of pixels. When extremely bright light is incident on the image sensor 90, the amount of electric charge is maximized. The maximum voltage of the pixel signal corresponds to the minimum amount of electric charge generated in the plurality of pixels. In a dark state in which light incident on the plurality of pixels can be neglected, the amount of electric charge is minimized. The second voltage may be the low level.

The difference between the two voltages of the reference signal is greater than or equal to a predetermined value. The difference may be the same as the difference between the voltage of the standard signal and the minimum voltage of the pixel signal. The reference signal has an amplitude of greater than or equal to the predetermined value.

The effective video signal is input into the multiplexer 93 in the effective period, and the reference signal is input into the multiplexer 93 in the horizontal blanking period. The multiplexer 93 outputs the effective video signal to the transmission circuit 91 in the effective period and outputs the reference signal to the transmission circuit 91 in the horizontal blanking period. The video signal includes the effective video signal and the reference signal.

The effective video signal is input into the transmission circuit 91 in the effective period, and the reference signal is input into the transmission circuit 91 in the horizontal blanking period. The transmission circuit 91 transmits the effective video signal to the AFE 50 in the effective period and transmits the reference signal to the AFE 50 in the horizontal blanking period.

The video signal is input into the binary circuit 510 of the phase adjustment circuit 51. The effective video signal is input into the binary circuit 510 in the effective period, and the reference signal is input into the binary circuit 510 in the horizontal blanking period. The binary circuit 510 detects an edge of the video signal in the effective period by using the effective video signal. The binary circuit 510 detects an edge of the video signal in the horizontal blanking period by using the reference signal.

Figure 12:
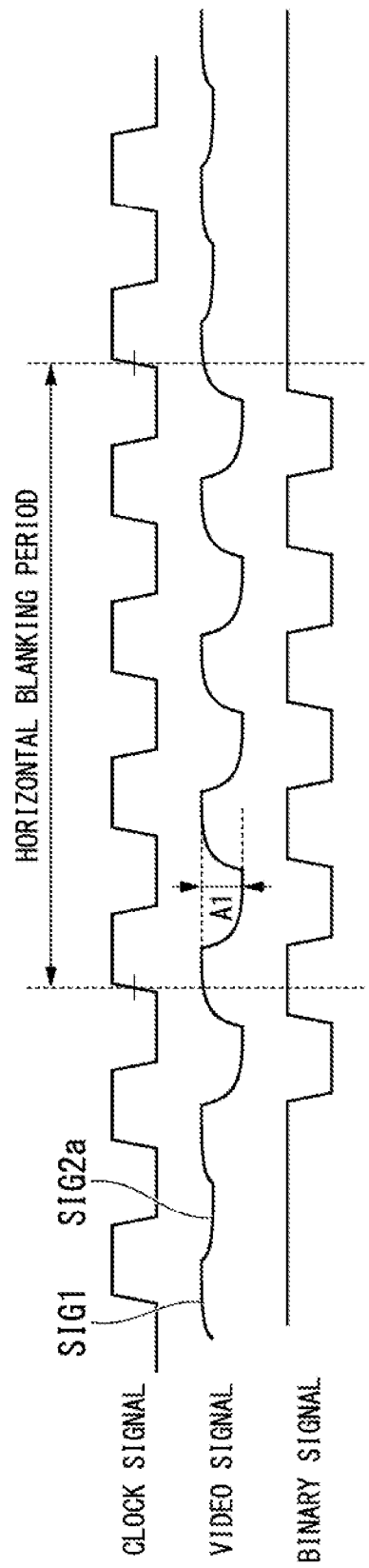
FIG. 12 is a timing chart showing waveforms of signals in the endoscope system according to the fifth embodiment of the present invention.

FIG. 12 shows waveforms of the clock signal, the video signal, and the binary signal. The horizontal direction in FIG. 12 indicates time, and the vertical direction in FIG. 12 indicates a voltage of each signal.

In the horizontal blanking period, the video signal includes the reference signal. The reference signal has a predetermined amplitude A1.

In a dark state, the video signal includes a pixel signal SIG2a. The voltage of the pixel signal SIG2a is almost the same as that of a standard signal SIG1. The binary circuit 510 may fail to detect an edge between the standard signal SIG1 and the pixel signal SIG2a.

In the horizontal blanking period, the reference signal always has an edge. Therefore, the binary circuit 510 can easily detect an edge of the reference signal. The phase adjustment circuit 51 can generate the sampling signal having an accurate phase.

The phase adjustment circuit 51 may be changed to the phase adjustment circuit 51a shown in FIG. 5, the phase adjustment circuit 51b shown in FIG. 6, or the phase adjustment circuit 51c shown in FIG. 7.

Sixth Embodiment

Figure 13:
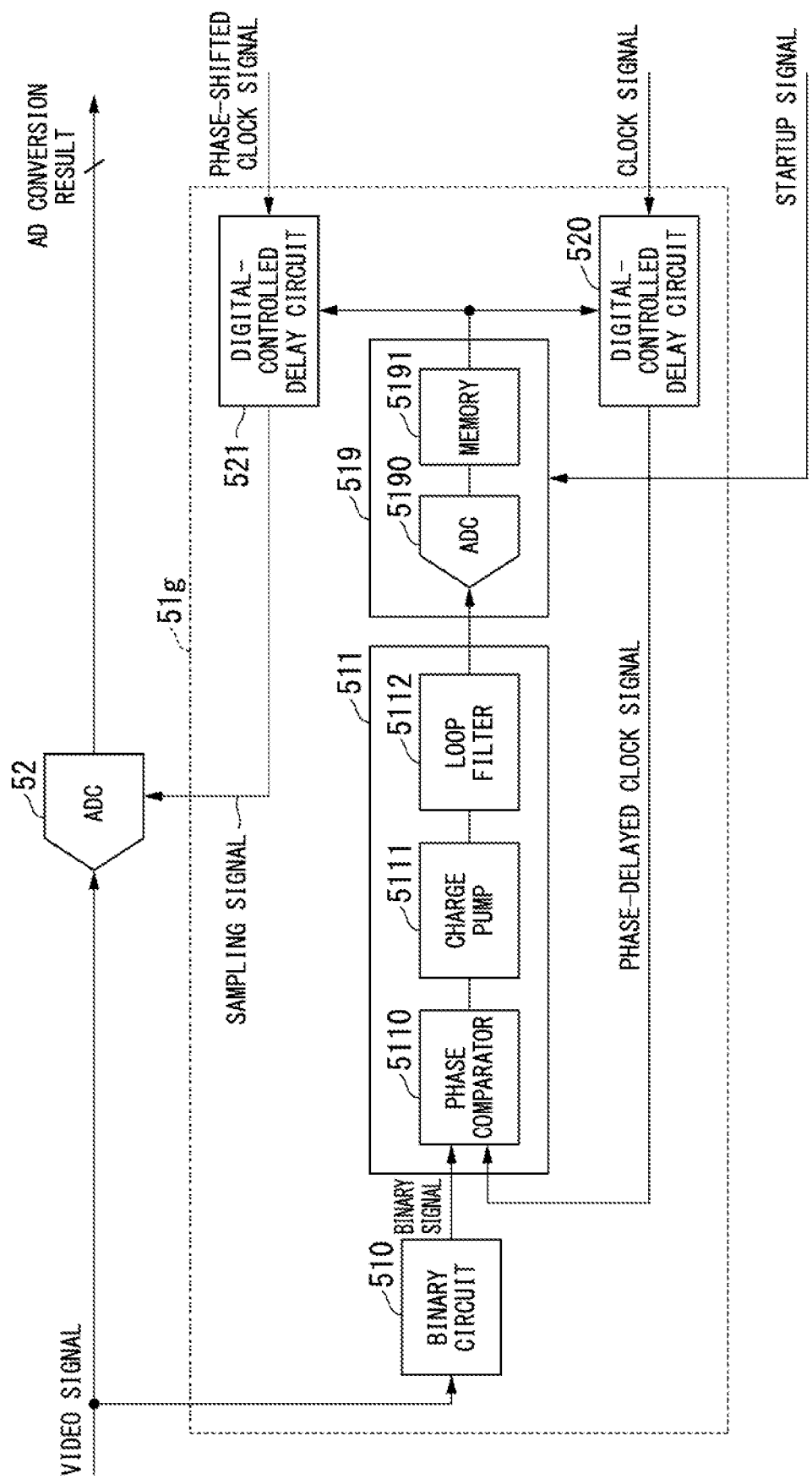
FIG. 13 is a block diagram showing a configuration of a binary circuit included in an endoscope system according to a sixth embodiment of the present invention.

FIG. 13 shows a configuration of a phase adjustment circuit 51g according to a sixth embodiment of the present invention. The phase adjustment circuit 51g shown in FIG. 13 includes a binary circuit 510, a delay time control circuit 511, a control-voltage-holding circuit 519, a digital-controlled delay circuit 520 (first digital-controlled delay circuit), and a digital-controlled delay circuit 521 (second digital-controlled delay circuit). The control-voltage-holding circuit 519 includes an ADC 5190 and a memory 5191. The same configuration as that shown in FIG. 3 will not be described.

A schematic configuration of the phase adjustment circuit 51g will be described. The memory 5191 stores digital information indicating a first delay amount when the delay time control circuit 511 causes the phase of the binary signal and the phase of the phase-delayed clock signal to match each other. The digital-controlled delay circuit 520 generates the phase-delayed clock signal having a later phase than that of the clock signal by the first delay amount indicated by the digital information. The digital-controlled delay circuit 521 generates a sampling signal having a later phase than that of the clock signal by a second delay amount in accordance with a predetermined shift amount and the first delay amount indicated by the digital information.

A detailed configuration of the phase adjustment circuit 51g will be described. A loop filter 5112 of the delay time control circuit 511 outputs a control voltage to the control-voltage-holding circuit 519. The control voltage is input into the ADC 5190. The ADC 5190 performs AD conversion. The ADC 5190 converts the analog control voltage into the digital information. The ADC 5190 outputs the digital information to the memory 5191. The memory 5191 stores the digital information. The control voltage indicated by the digital information corresponds to the first delay amount. The memory 5191 continues to hold the same digital information until the control voltage is updated. The memory 5191 outputs the digital information to the digital-controlled delay circuit 520 and the digital-controlled delay circuit 521.

The clock signal is input into the digital-controlled delay circuit 520. The digital-controlled delay circuit 520 generates the phase-delayed clock signal by delaying the phase of the clock signal by the first delay amount indicated by the digital information. The first delay amount is controlled by the digital information input into the digital-controlled delay circuit 520. The digital-controlled delay circuit 520 outputs the phase-delayed clock signal to the delay time control circuit 511.

The phase-shifted clock signal is input into the digital-controlled delay circuit 521. The digital-controlled delay circuit 521 generates the sampling signal by delaying the phase of the phase-shifted clock signal by the first delay amount indicated by the digital information. The first delay amount is controlled by the digital information input into the digital-controlled delay circuit 521. The digital-controlled delay circuit 521 includes the same configuration as that of the digital-controlled delay circuit 520. Therefore, the first delay amount given to the phase-shifted clock signal by the digital-controlled delay circuit 521 is the same as that given to the clock signal by the digital-controlled delay circuit 520. The digital-controlled delay circuit 521 outputs the sampling signal to the ADC 52.

The signal generation circuit 61 of the processor 6 generates a startup signal indicating a startup period and outputs the startup signal to the control-voltage-holding circuit 519. For example, the startup period is started when the power source of the endoscope system 1 is turned on. The startup period is completed before a high-frequency generator such as an electric scalpel starts to operate.

The ADC 5190 performs the AD conversion in the startup period, and the memory 5191 stores the digital information in the startup period. The ADC 5190 may stop the AD conversion after the startup period is completed.

After the startup period is completed, the processor 6 may determine whether the high-frequency generator is operating. When the processor 6 determines that the high-frequency generator is not operating, the processor 6 may cause the control-voltage-holding circuit 519 to operate.

When the high-frequency generator is operating, there is a possibility that noise generated by the high-frequency generator is mixed into the video signal. Therefore, the binary circuit 510 may fail to accurately detect an edge of the video signal.

The control-voltage-holding circuit 519 operates in a period during which the high-frequency generator is not operating. The digital-controlled delay circuit 520 generates the phase-delayed clock signal on the basis of the digital information stored on the memory 5191 in the period. The digital-controlled delay circuit 521 generates the sampling signal on the basis of the digital information stored on the memory 5191 in the period. Therefore, the phase adjustment circuit 51g can generate the sampling signal having an accurate phase without being influenced by noise.

The phase adjustment circuit 51a shown in FIG. 5, the phase adjustment circuit 51b shown in FIG. 6, or the phase adjustment circuit 51c shown in FIG. 7 may include the control-voltage-holding circuit 519.

Seventh Embodiment

Figure 14:
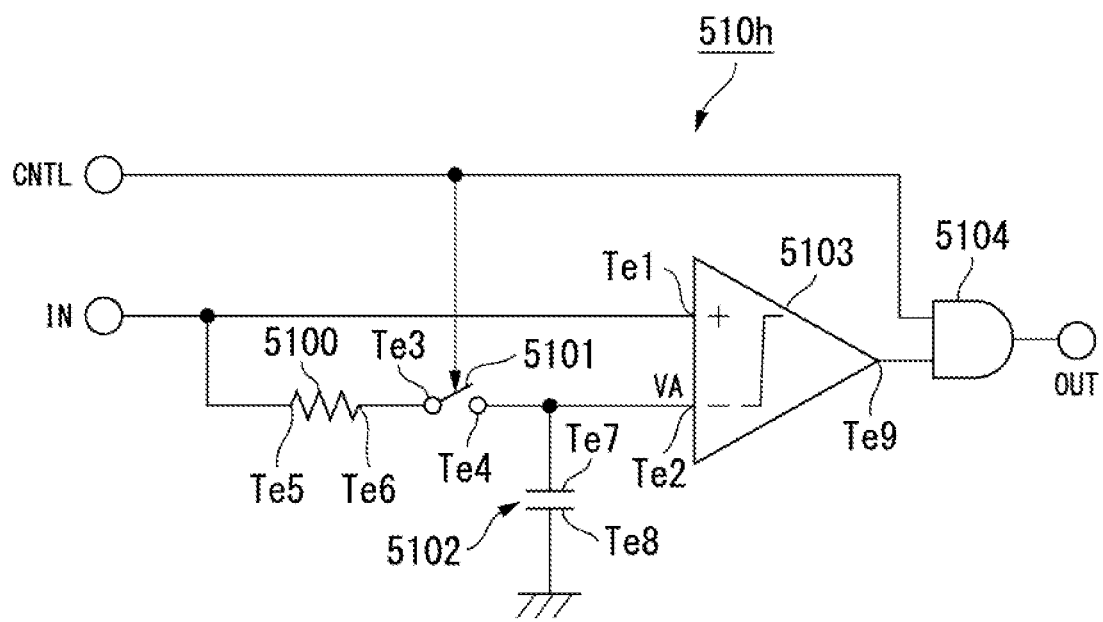
FIG. 14 is a circuit diagram showing a configuration of a binary circuit included in an endoscope system according to a seventh embodiment of the present invention.

FIG. 14 shows a configuration of a binary circuit 510h according to a seventh embodiment of the present invention. In the phase adjustment circuit 51 shown in FIG. 11, the binary circuit 510 is changed to the binary circuit 510h shown in FIG. 14. The binary circuit 510h shown in FIG. 14 includes a resistor 5100, a switch 5101, a condenser 5102, a comparator 5103, and an AND circuit 5104.

A schematic configuration of the binary circuit 510h will be described. The comparator 5103 includes a first terminal Te1 and a second terminal Te2. The video signal is input into the first terminal Te1. The comparator 5103 generates a binary signal on the basis of a result of comparing the voltage of the first terminal Te1 with the voltage of the second terminal Te2. The video signal is input into the resistor 5100. The switch 5101 includes a third terminal Te3 and a fourth terminal Te4 and goes into any one of an ON state and an OFF state. The video signal output from the resistor 5100 is input into the third terminal Te3, and the fourth terminal Te4 is electrically connected to the second terminal Te2. The third terminal Te3 and the fourth terminal Te4 are electrically connected to each other in the ON state. The third terminal Te3 and the fourth terminal Te4 are electrically insulated from each other in the OFF state. The condenser 5102 is electrically connected to the second terminal Te2 and the fourth terminal Te4. After the state of the switch 5101 changes to the ON state, the switch 5101 goes into the OFF state. When the state of the switch 5101 is the OFF state, the comparator 5103 generates a binary signal.

A detailed configuration of the binary circuit 510h will be described. The resistor 5100 is a resistance element. The resistor 5100 includes a fifth terminal Te5 and a sixth terminal Te6. A video signal IN is input into the first terminal Te1 and the fifth terminal Te5. The third terminal Te3 is electrically connected to the sixth terminal Te6. The video signal output from the sixth terminal Te6 is input into the third terminal Te3.

The states of the switch 5101 are switched between the ON state and the OFF state. When the state of the switch 5101 is the ON state, the third terminal Te3 and the fourth terminal Te4 are electrically connected to each other. When the state of the switch 5101 is the OFF state, the third terminal Te3 and the fourth terminal Te4 are electrically insulated from each other. The state of the switch 5101 is controlled on the basis of a control signal CNTL. The control signal CNTL has the high level or the low level. For example, the signal generation circuit 61 of the processor 6 generates the control signal CNTL and outputs the control signal CNTL to the binary circuit 510h.

The condenser 5102 is a capacitance element. The condenser 5102 includes a seventh terminal Te7 and an eighth terminal Te8. The seventh terminal Te7 is electrically connected to the second terminal Te2 and the fourth terminal Te4. The eighth terminal Te8 is connected to the ground.

When the state of the switch 5101 is the ON state, the video signal output from the sixth terminal Te6 is input into the seventh terminal Te7 via the switch 5101. When the state of the switch 5101 changes from the ON state to the OFF state, the condenser 5102 holds the voltage of the video signal. While the state of the switch 5101 is the OFF state, the condenser 5102 outputs the voltage to the second terminal Te2.

The comparator 5103 includes a ninth terminal Te9 in addition to the first terminal Te1 and the second terminal Te2. The first terminal Te1 is a non-inverting input terminal, and the second terminal Te2 is an inverting input terminal. The comparator 5103 outputs, from the ninth terminal Te9, a signal in accordance with the difference between the voltage of the first terminal Te1 and the voltage of the second terminal Te2. The signal output from the ninth terminal Te9 has the high level or the low level. The comparator 5103 may be a hysteresis comparator.

The AND circuit 5104 includes two input terminals and one output terminal. The control signal CNTL is input into one of the two input terminals, and the signal output from the ninth terminal Te9 is input into the other of the two input terminals. The AND circuit 5104 performs an AND operation of the signals input into the two input terminals and outputs a binary signal OUT indicating a result of the operation to the delay time control circuit 511.

Figure 15:
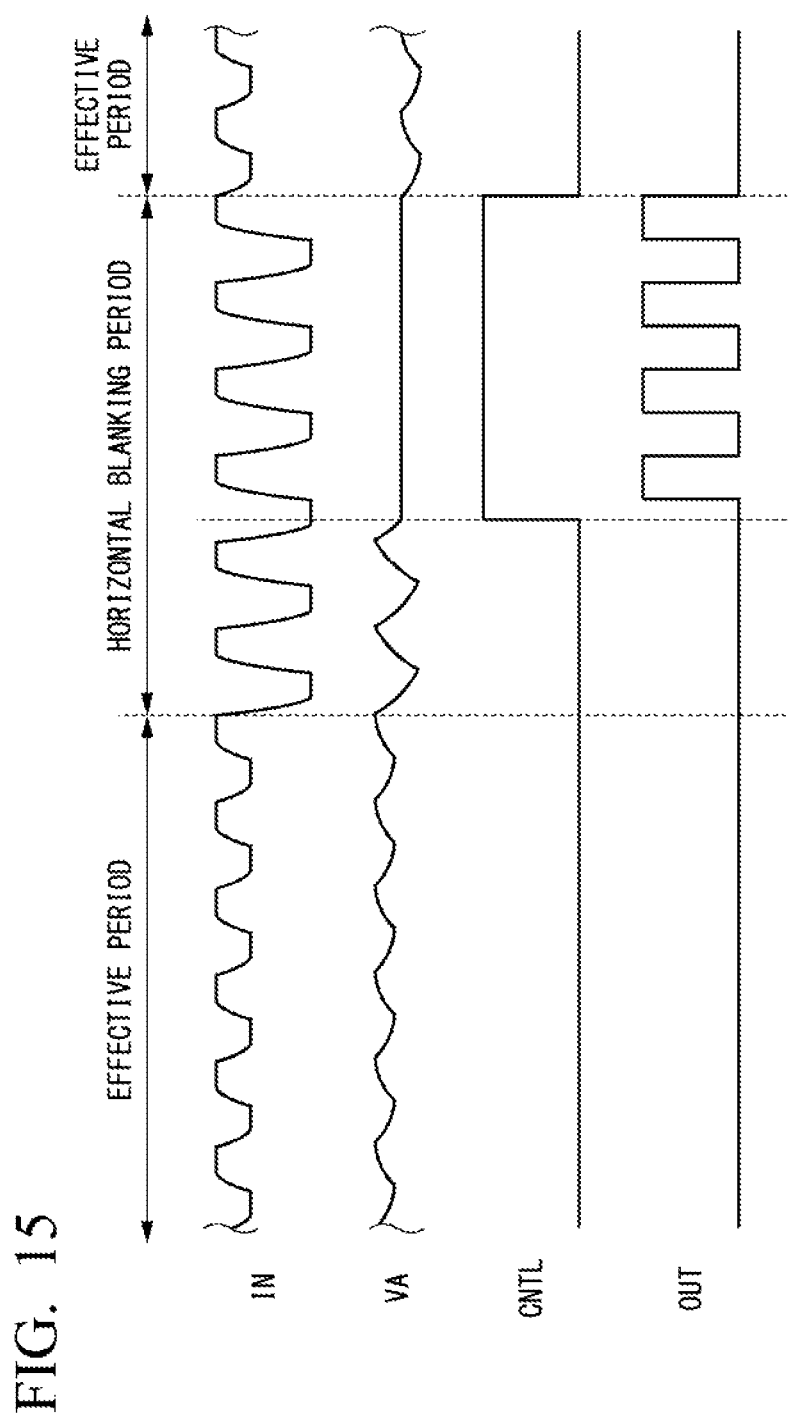
FIG. 15 is a timing chart showing waveforms of signals in the binary circuit included in the endoscope system according to the seventh embodiment of the present invention.

FIG. 15 shows waveforms of the video signal IN, a voltage VA of the second terminal Te2, the control signal CNTL, and the binary signal OUT. The horizontal direction in FIG. 15 indicates time, and the vertical direction in FIG. 15 indicates a voltage of each signal.

The video signal IN includes a standard signal and a pixel signal in an effective period. The standard signal and the pixel signal appear one after the other. The voltage of the control signal CNTL is the low level in the effective period. Therefore, the AND circuit 5104 outputs the binary signal OUT having the low level.

The video signal IN includes a reference signal in a horizontal blanking period following the effective period. The reference signal has the high level or the low level. When the horizontal blanking period is started, the voltage of the control signal CNTL is the low level. At this time, the state of the switch 5101 is the ON state. The reference signal is input into the condenser 5102 via the resistor 5100 and the switch 5101.

When the voltage of the reference signal changes from the high level to the low level in the horizontal blanking period, the voltage of the control signal CNTL changes from the low level to the high level. At this time, the state of the switch 5101 changes from the ON state to the OFF state. The condenser 5102 holds the voltage of the reference signal and outputs the voltage to the second terminal Te2.

The comparator 5103 outputs, from the ninth terminal Te9, a signal in accordance with the difference between the voltage of the reference signal input into the first terminal Te1 and the voltage VA input into the second terminal Te2 in the horizontal blanking period. The control signal CNTL and the signal output from the ninth terminal Te9 are input into the AND circuit 5104. The AND circuit 5104 outputs the binary signal OUT on the basis of the two signals.

When the horizontal blanking period is completed, the voltage of the control signal CNTL changes from the high level to the low level. At this time, the state of the switch 5101 changes from the OFF state to the ON state. After the horizontal blanking period is completed, the effective period is started.

In the example shown in FIG. 15, when the voltage of the reference signal changes from the high level to the low level in the horizontal blanking period, the state of the switch 5101 changes from the ON state to the OFF state. When the voltage of the reference signal changes from the low level to the high level in the horizontal blanking period, the state of the switch 5101 may change from the ON state to the OFF state.

In the example shown in FIG. 15, the state of the switch 5101 changes from the ON state to the OFF state in the horizontal blanking period. The state of the switch 5101 may change from the ON state to the OFF state in the effective period. In this case, the camera unit 9*f* does not need to include the reference signal generation circuit 92 or the multiplexer 93.

While the state of the switch 5101 is the OFF state, the voltage of the reference signal input into the second terminal Te2 does not change. The DC voltage of the highly stable reference signal is input into the second terminal Te2. Therefore, the comparator 5103 can generate a highly accurate binary signal in synchronization with a timing at which the voltage of the reference signal input into the first terminal Te1 changes.

Eighth Embodiment

Figure 16:
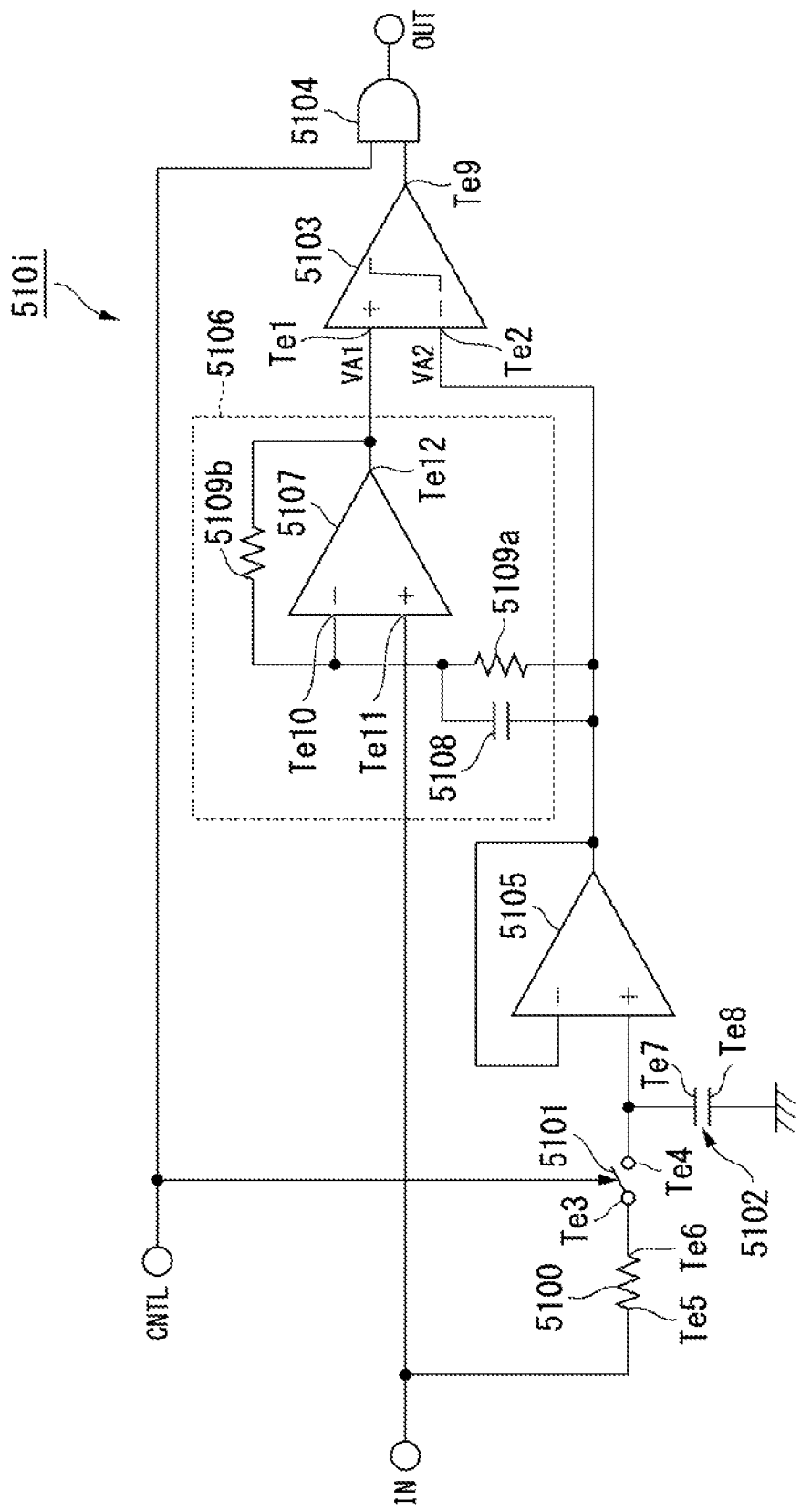
FIG. 16 is a circuit diagram showing a configuration of a binary circuit included in an endoscope system according to an eighth embodiment of the present invention.

FIG. 16 shows a configuration of a binary circuit 510*i* according to an eighth embodiment of the present invention. In the phase adjustment circuit 51 shown in FIG. 11, the binary circuit 510 is changed to the binary circuit 510*i* shown in FIG. 16. The binary circuit 510*i* shown in FIG. 16 includes a resistor 5100, a switch 5101, a condenser 5102, a comparator 5103, an AND circuit 5104, a voltage follower 5105, and a differentiation-amplification circuit 5106. The same configuration as that shown in FIG. 14 will not be described.

A schematic configuration of the binary circuit 510*i* will be described. The differentiation-amplification circuit 5106 performs differentiation and amplification on the video signal IN. The video signal IN is input into the resistor 5100 and the differentiation-amplification circuit 5106. The video signal on which the differentiation and the amplification are performed is output from the differentiation-amplification circuit 5106 and is input into the first terminal Te1.

A detailed configuration of the binary circuit 510*i* will be described. The voltage follower 5105 is disposed between the seventh terminal Te7 and the second terminal Te2. The voltage output from the seventh terminal Te7 is input into the second terminal Te2 via the voltage follower 5105.

The differentiation-amplification circuit 5106 has a differentiation function and an amplification function. The differentiation-amplification circuit 5106 includes an operational amplifier 5107, a condenser 5108, a resistor 5109*a*, and a resistor 5109*b*.

The operational amplifier 5107 includes a tenth terminal Te10, an eleventh terminal Te11, and a twelfth terminal Te12. The tenth terminal Te10 is an inverting input terminal, and the eleventh terminal Te11 is a non-inverting input terminal. The video signal IN is input into the eleventh terminal Te11.

The condenser 5108 and the resistor 5109*a* are disposed between the second terminal Te2 and the tenth terminal Te10. The condenser 5108 and the resistor 5109*a* are connected in parallel to each other. One of two terminals of the condenser 5108 is electrically connected to the second terminal Te2, and the other of the two terminals of the condenser 5108 is electrically connected to the tenth terminal Te10. One of two terminals of the resistor 5109*a* is electrically connected to the second terminal Te2, and the other of the two terminals of the resistor 5109*a* is electrically connected to the tenth terminal Te10.

The resistor 5109*b* is disposed between the tenth terminal Te10 and the twelfth terminal Te12. One of two terminals of the resistor 5109*b* is electrically connected to the tenth terminal Te10, and the other of the two terminals of the resistor 5109*b* is electrically connected to the twelfth terminal Te12. The differentiation-amplification circuit 5106 constituted by the operational amplifier 5107, the resistor 5109*a*, the resistor 5109*b*, and the condenser 5108 outputs, from the twelfth terminal Te12, a signal generated by performing the differentiation and the amplification on the video signal IN. The twelfth terminal Te12 is electrically connected to the first terminal Te1. The signal output from the twelfth terminal Te12 is input into the first terminal Te1.

The differentiation-amplification circuit 5106 highlights a rising rate and a falling rate of the video signal IN, thus adjusting the waveform of the video signal IN. Since the differentiation-amplification circuit 5106 includes the resistor 5109*a*, the differentiation-amplification circuit 5106 can amplify a signal having a high frequency.

Figure 17:
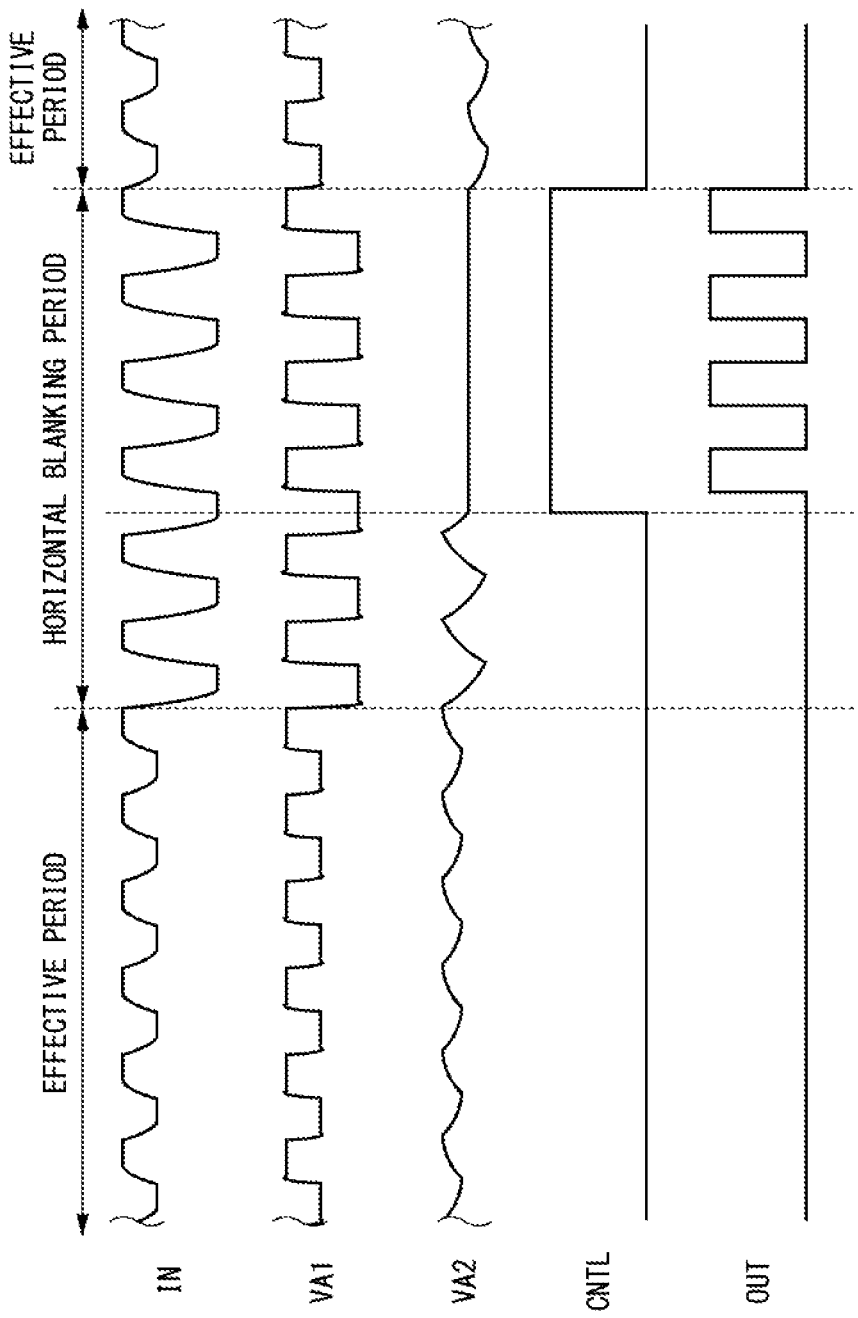
FIG. 17 is a timing chart showing waveforms of signals in the binary circuit included in the endoscope system according to the eighth embodiment of the present invention.
Figure 18:
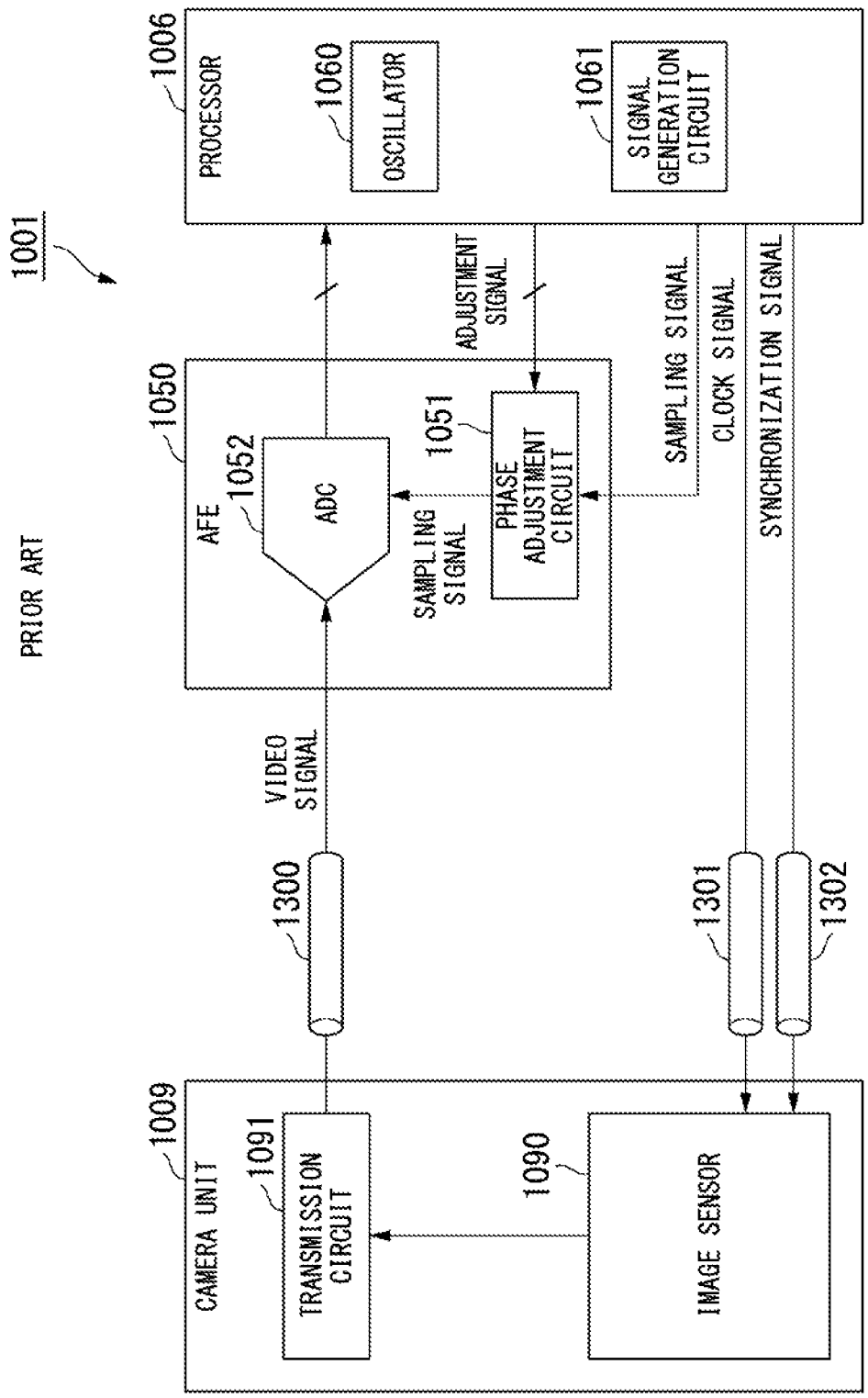
FIG. 18 is a block diagram showing a configuration of an endoscope system of the prior art.
Figure 19:
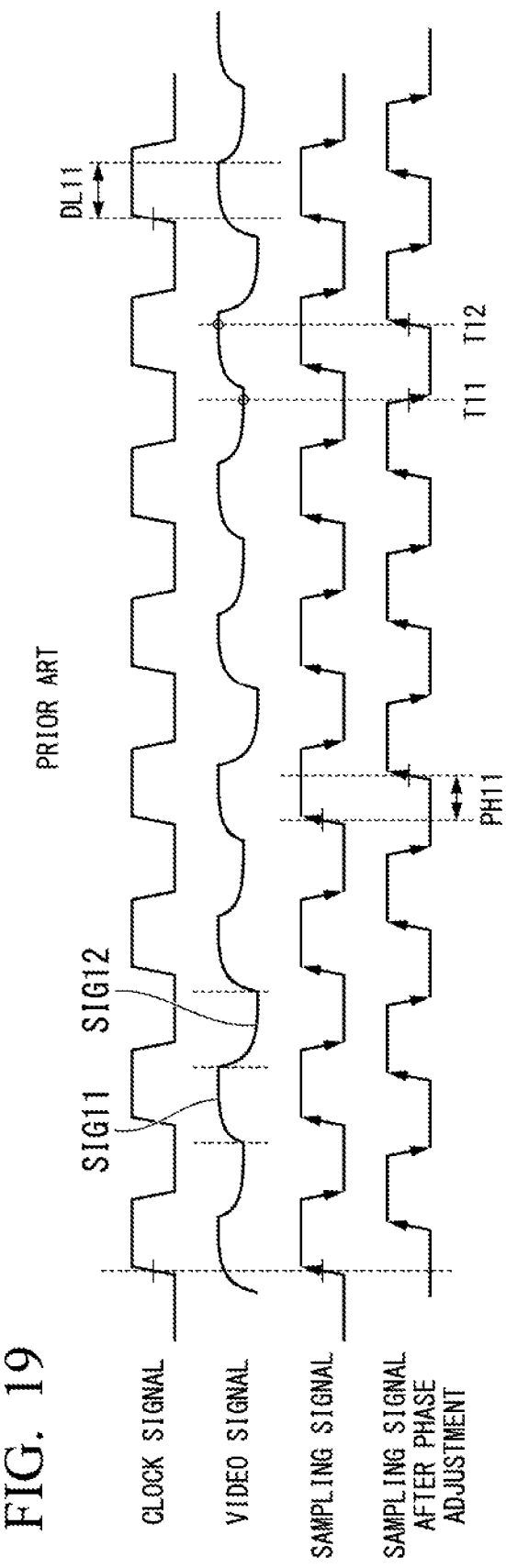
FIG. 19 is a timing chart showing waveforms of signals in the endoscope system of the prior art.

FIG. 17 shows waveforms of the video signal IN, a voltage VA1 of the first terminal Te1, a voltage VA2 of the second terminal Te2, the control signal CNTL, and the binary signal OUT. The horizontal direction in FIG. 17 indicates time, and the vertical direction in FIG. 17 indicates a voltage of each signal. The same parts as those shown in FIG. 15 will not be described.

The differentiation-amplification circuit 5106 performs the differentiation and the amplification on the video signal IN and outputs the processed video signal to the first terminal Te1. The voltage VA1 rises and falls faster than the video signal IN.

The comparator 5103 outputs a signal in accordance with the difference between the voltage VA1 of the first terminal Te1 and the voltage VA2 of the second terminal Te2 from the ninth terminal Te9 in the horizontal blanking period. The control signal CNTL and the signal output from the ninth terminal Te9 are input into the AND circuit 5104. The AND circuit 5104 outputs the binary signal OUT on the basis of the two signals.

In the example shown in FIG. 17, when the voltage of the reference signal changes from the high level to the low level in the horizontal blanking period, the state of the switch 5101 changes from the ON state to the OFF state. When the voltage of the reference signal changes from the low level to the high level in the horizontal blanking period, the state of the switch 5101 may change from the ON state to the OFF state.

In the example shown in FIG. 17, the state of the switch 5101 changes from the ON state to the OFF state in the horizontal blanking period. The state of the switch 5101 may change from the ON state to the OFF state in the effective period. In this case, the camera unit 9f does not need to include the reference signal generation circuit 92 or the multiplexer 93.

While the state of the switch 5101 is the OFF state, the voltage of the reference signal input into the second terminal Te2 does not change. The DC voltage of the highly stable reference signal is input into the second terminal Te2. In addition, the reference signal of which the rising rate and falling rate are highlighted is input into the first terminal Te1. Therefore, the comparator 5103 can generate an accurate binary signal in synchronization with a timing at which the voltage of the reference signal input into the first terminal Te1 changes.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A phase adjustment circuit configured to generate a sampling signal used for capturing a video signal at a later timing than a timing indicated by a clock signal, the phase adjustment circuit comprising:
   a binary circuit configured to detect an edge of the video signal and output a binary signal having a voltage that changes at a timing of the detected edge;
   a phase-delayed clock signal generation circuit configured to generate a phase-delayed clock signal having a later phase than a phase of the clock signal by a first delay amount;
   a delay time control circuit configured to cause a phase of the binary signal and the phase of the phase-delayed clock signal to match each other by adjusting the first delay amount on the basis of the binary signal and the phase-delayed clock signal; and
   a sampling signal generation circuit configured to generate the sampling signal having a later phase than the phase of the clock signal by a second delay amount, wherein the second delay amount is in accordance with both a phase shift amount, which is based on the timing indicated by the clock signal, and the first delay amount adjusted by the delay time control circuit.

2. The phase adjustment circuit according to claim 1, wherein the sampling signal generation circuit is configured to receive the clock signal and generate the sampling signal by adding the second delay amount to the clock signal, and
   wherein the phase-delayed clock signal generation circuit is configured to receive the sampling signal generated by the sampling signal generation circuit and generate the phase-delayed clock signal by changing the phase of the sampling signal by the shift amount.

3. The phase adjustment circuit according to claim 1, wherein the phase-delayed clock signal generation circuit is configured to receive the clock signal and generate the phase-delayed clock signal by adding the first delay amount to the clock signal, and
   wherein the sampling signal generation circuit is configured to receive the phase-delayed clock signal generated by the phase-delayed clock signal generation circuit and generate the sampling signal by changing the phase of the phase-delayed clock signal by the shift amount.

4. The phase adjustment circuit according to claim 1, wherein the sampling signal generation circuit is configured to receive the clock signal having a higher frequency than a frequency of the video signal and generate the sampling signal having almost the same frequency as the frequency of the video signal by adding the second delay amount to the clock signal and by reducing the frequency of the clock signal, and
   wherein the phase-delayed clock signal generation circuit is configured to receive the sampling signal generated by the sampling signal generation circuit and generate the phase-delayed clock signal by changing the phase of the sampling signal by the shift amount by using a shift register.

5. The phase adjustment circuit according to claim 1, further comprising a delay circuit configured to:
   receive the phase-delayed clock signal generated by the phase-delayed clock signal generation circuit;
   add a third delay amount to the phase-delayed clock signal,
       wherein the third delay amount is a difference between a phase of the video signal input into the binary circuit and a phase of the binary signal; and
   output the phase-delayed clock signal to which the third delay amount has been added to the delay time control circuit.

6. The phase adjustment circuit according to claim 1, wherein the sampling signal generation circuit is configured to output the sampling signal to a video-signal-capturing circuit configured to capture the video signal on the basis of the sampling signal, and
   wherein the phase adjustment circuit further comprises a delay circuit configured to:
   add a third delay amount to the video signal,
       wherein the third delay amount is a difference between a phase of the video signal input into the binary circuit and a phase of the binary signal; and
   output the video signal to which the third delay amount has been added to the video-signal-capturing circuit.

7. The phase adjustment circuit according to claim 1, wherein the video signal includes a reference signal transmitted in a blanking period, and
   wherein the binary circuit is configured to detect the edge of the video signal by using the reference signal.

8. The phase adjustment circuit according to claim 1, wherein the video signal includes a first signal having a predetermined voltage and a second signal having a voltage that fluctuates, and
   wherein the first signal and the second signal appear one after the other.

9. The phase adjustment circuit according to claim 1, further comprising a memory configured to store digital information indicating the first delay amount when the delay time control circuit causes the phase of the binary signal and the phase of the phase-delayed clock signal to match each other,
   wherein the phase-delayed clock signal generation circuit comprises a first digital-controlled delay circuit configured to generate the phase-delayed clock signal having a later phase than the phase of the clock signal by the first delay amount indicated by the digital information, and wherein the sampling signal generation circuit comprises a second digital-controlled delay circuit configured to generate the sampling signal having a later phase than the phase of the clock signal by the second delay amount in accordance with the shift amount and the first delay amount indicated by the digital information.

10. The phase adjustment circuit according to claim 1, wherein the binary circuit comprises:
- a comparator that comprises a first terminal to which the video signal is input and a second terminal and is configured to generate the binary signal on the basis of a result of comparing a voltage of the first terminal with a voltage of the second terminal;
- a resistor into which the video signal is input;
- a switch that comprises a third terminal and a fourth terminal and is configured to go into any one of an ON state and an OFF state,
    - wherein the video signal output from the resistor is input into the third terminal,
    - wherein the fourth terminal is electrically connected to the second terminal,
    - wherein the third terminal and the fourth terminal are electrically connected to each other in the ON state, and
    - wherein the third terminal and the fourth terminal are electrically insulated from each other in the OFF state; and
- a condenser electrically connected to the second terminal and the fourth terminal, wherein, after a state of the switch changes to the ON state, the switch is configured to go into the OFF state, and wherein, when the state of the switch is the OFF state, the comparator is configured to generate the binary signal.

11. The phase adjustment circuit according to claim 10, wherein the binary circuit further comprises a differentiation-amplification circuit configured to perform differentiation and amplification on the video signal, wherein the video signal is input into the resistor and the differentiation-amplification circuit, and wherein the video signal on which the differentiation and the amplification are performed is output from the differentiation-amplification circuit and is input into the first terminal.

12. An endoscope system, comprising:
a scope comprising an image sensor;
a video-signal-capturing circuit; and
the phase adjustment circuit according to claim 1,
wherein the image sensor is disposed in a distal end of the scope and is configured to generate the video signal,
wherein the scope and the video-signal-capturing circuit are connected to each other by a signal line configured to transfer the video signal output from the image sensor, and
wherein the video-signal-capturing circuit is configured to capture the video signal on the basis of the sampling signal.

* * * * *